United States Patent [19]
Johnson et al.

[11] Patent Number: 6,103,920
[45] Date of Patent: Aug. 15, 2000

[54] OLEFIN POLYMERIZATION PROCESS

[75] Inventors: Lynda Kaye Johnson, Wilmington; Jerald Feldman, Hockessin; Kristina Ann Kreutzer, Wilmington; Stephan James Mclain, Wilmington; Alison Margaret Anne Bennett, Wilmington; Edward Bryan Coughlin, Wilmington, all of Del.; Dennis Scott Donald, Mendenhall, Pa.; Lissa Taka Jennings Nelson, Boothwyn, Pa.; Anju Parthasarathy, Glenmoore, Pa.; Xing Shen, La Jolla, Calif.; Wilson Tam, Boothwyn, Pa.; Yueli Wang, Wilmington, Del.

[73] Assignee: E. I. du Pont de Nemours and Company, Wilmington, Del.

[21] Appl. No.: 08/899,032

[22] Filed: Jul. 23, 1997

Related U.S. Application Data

[62] Division of application No. 08/671,392, Jun. 27, 1996, Pat. No. 5,714,556.
[60] Provisional application No. 60/000,747, Jun. 30, 1995.

[51] Int. Cl.[7] .................................................. C07F 15/04
[52] U.S. Cl. ................. 556/140; 556/21; 549/3; 549/206; 540/465; 540/541; 544/225; 502/155
[58] Field of Search ....................... 556/140, 21; 540/465, 540/541; 544/225; 549/3, 206; 502/155

[56] References Cited

U.S. PATENT DOCUMENTS

| | | | |
|---|---|---|---|
| 3,379,706 | 4/1968 | Wilke | 260/943 |
| 3,432,530 | 3/1969 | Mulheim | 260/429 |
| 3,637,636 | 1/1972 | Bauer et al. | 260/94.9 C |
| 3,676,523 | 7/1972 | Mason | 260/683.15 D |
| 3,719,653 | 3/1973 | Dawans | 260/94.3 |
| 4,716,205 | 12/1987 | Klabunde | 526/115 |
| 5,198,512 | 3/1993 | Jackson et al. | 526/130 |
| 5,322,910 | 6/1994 | Wu | 526/107 |
| 5,332,794 | 7/1994 | Ohtsu et al. | 526/169.1 |
| 5,395,811 | 3/1995 | Novak et al. | 502/152 |
| 5,461,126 | 10/1995 | Knudsen et al. | 526/96 |
| 5,468,819 | 11/1995 | Goodall et al. | 526/171 |

FOREIGN PATENT DOCUMENTS

| | | |
|---|---|---|
| 0 454 231 A2 | 4/1991 | European Pat. Off. |
| 1 793 788 | 11/1974 | Germany |
| 44 15 725 A1 | 11/1994 | Germany |
| WO 95/14048 | 5/1995 | WIPO |
| WO 96/23010 | 8/1996 | WIPO |

OTHER PUBLICATIONS

Gunther, Wilke, Contributions to Organo–Nickel Chemistry. Angew. Chem. Int. Ed. Engl., vol. 27, pp. 185–206, 1988.

Rudolf Taube, et al., The Catalysis of Stereospecific Butadiene polymerization by Allyl Nickel and Allyl Lanthanide Complexes—A Mechanistic Comparison. Macro–molecular Symposia, vol. 89, pp. 397–409, 1995.

Stransky et al., J. Organomet. Chem., vol. 270, No. 3, pp. 357–363, 1984.

Guerrieri et al., Chemical Abstracts, vol. 68, Abstract No. 13160, 1968.

Martin A. Robinson, et al. Complexes Derived from Strong Field Ligands, XVII. Electronic Spectra of Octahedral Nickel(II) Complexes with Ligands of the α–Diimine and Closely Related Classes. Inorganic chemistry, 2. 1178–1181. May 1963.

Lynda K. Johnson, et al., New Pd(II)–and Ni(II)–Based Catalysts for Polymerization of Ethylene and α–Olefins. J. Am. Chem. Soc., 117, 6414–6415, 1995.

*Primary Examiner*—Porfirio Nazario-Gonzalez
*Attorney, Agent, or Firm*—Joel D. Citron; Craig H. Evans

[57] ABSTRACT

Disclosed herein is a process for the polymerization of ethylene, norbornenes and styrenes, by contacting in solution a selected nickel compound and a selected compound which is or can coordinated to the nickel with the olefin(s). The polymers produced are useful for films and molding resins.

44 Claims, No Drawings

OLEFIN POLYMERIZATION PROCESS

This is a division of application Ser. No. 08/671,392, filed Jun. 27, 1996, now U.S. Pat. No. 5,714,556, which claims the benefit of U.S. Provisional Application Ser. No. 60/000,747, filed Jun. 30, 1995.

FIELD OF THE INVENTION

This invention concerns a process for the preparation of polyolefins by coordination polymerization of ethylene, styrene or norbornene by a nickel compound coordinated to a selected ligand.

TECHNICAL BACKGROUND

Polyolefins are very important items of commerce, being used for myriad uses, such as molding resins, films, ropes, composites, fibers, elastomers, etc. Suitability for any particular use is dependent on the polymer properties, for instance whether the polymer is elastomeric or thermoplastic. One method of polymerization of these olefins is by coordination polymerization, use of a polymerization catalyst containing a transition metal, the metal usually being thought of as coordinating to one or more species during the polymerization process.

Whether any particular transition metal compound is an olefin polymerization catalyst usually depends on the metal chosen and what is coordinated (such as various ligands) to the metal before and during the polymerization. Various transition metal compounds may or may not be active catalysts for a particular (type of) olefin, and the resulting polymer structures may vary. Other factors such as the efficiency and rate of polymerization may vary. Therefore, new transition metal catalysts for olefin polymerizations are constantly being sought.

SUMMARY OF THE INVENTION

This invention concerns a process for the polymerization of an olefin, comprising:

(a) contacting a polymerizable monomer consisting essentially of ethylene, a norbornene or a styrene, and a catalyst system comprising the product of mixing in solution a zerovalent tricoordinate or tetracoordinate nickel compound (II) which has at least one labile ligand, and all ligands are neutral, an acid of the formula HX (IV), and a first compound selected from the group consisting of:

$Ar^1Q_n$ (III); $R^8R^{10}N$—$CR^4R^5(CR^6R^7)_{\overline{m}}$—$NR^8R^{10}$ (V);

$Ar^2$—$\overset{O}{\underset{\|}{C}}$—$NHR^{10}$ (XVI); (XVII);

$H_2N{\diagdown}{\diagup}CO_2H$ (XVIII); $H_2N{\diagdown}{\diagup}P(OH)_2$ (XIX);

(XX); (XXI); (XXIII); (XXII); (XXIV); $CO_2H$ (XXV); (XXVI);

$Ar^9HN$—$\overset{O}{\underset{\|}{S}}$—$NHAr^{10}$ (XXVII); $R^{22}R^{23}R^{24}P$ (XXVIII);

(XXXVI); and $R^8S$—$CR^4R^5(CR^6R^7)_{\overline{m}}$—$SR^8$ (XXXVII);

wherein:

X is a noncoordinating anion;

$Ar^1$ is an aromatic moiety with n free valencies, or diphenylmethyl;

each Q is —$NR^2R^{43}$ or —$CR^9$=$NR^3$;

n is 1 or 2;

E is 2-thienyl or 2-furyl;

each $R^2$ is independently hydrogen, benzyl, substituted benzyl, phenyl or substituted phenyl;

each $R^9$ is independently hydrogen or hydrocarbyl; and each $R^3$ is independently a monovalent aromatic moiety;

m is 1, 2 or 3;

$R^{43}$ is hydrogen or alkyl;

each $R^4$, $R^5$, $R^6$, and $R^7$ is independently hydrogen, hydrocarbyl or substituted hydrocarbyl;

each $R^8$ is independently hydrocarbyl or substituted hydrocarbyl containing 2 or more carbon atoms;

each $R^{10}$ is independently hydrogen, hydrocarbyl or substituted hydrocarbyl;

$Ar^2$ is an aryl moiety;

$R^{12}$, $R^{13}$, and $R^{14}$ are each independently hydrogen, hydrocarbyl, substituted hydrocarbyl or an inert functional group;

$R^{11}$ and $R^{15}$ are each independently hydrocarbyl, substituted hydrocarbyl or an inert functional group whose $E_s$ is about −0.4 or less;

each $R^{16}$ and $R^{17}$ is independently hydrogen or acyl containing 1 to 20 carbon atoms;

$Ar^3$ is an aryl moiety;

$R^{18}$ and $R^{19}$ are each independently hydrogen or hydrocarbyl;

$Ar^4$ is an aryl moiety;

$Ar^5$ and $Ar^6$ are each independently hydrocarby;

$Ar^7$ and $Ar^8$ are each independently an aryl moiety;

$Ar^9$ and $Ar^{10}$ are each independently an aryl moiety or —$CO_2R^{25}$, wherein $R^{25}$ is alkyl containing 1 to 20 carbon atoms;

$Ar^{11}$ is an aryl moiety;

$R^{41}$ is hydrogen or hydrocarbyl;

$R^{42}$ is hydrocarbyl or —C(O)—$NR^{41}$—$Ar^{11}$;

$R^{44}$ is aryl;

$R^{22}$ and $R^{23}$ are each independently phenyl groups substituted by one or more alkoxy groups, each alkoxy group containing 1 to 20 carbon atoms; and $R^{24}$ is alkyl containing 1 to 20 carbon atoms, or an aryl moiety.

This invention also concerns a catalyst for the polymerization of ethylene, a norbornene, or a styrene, comprising, the product of mixing in solution a zerovalent tricoordinate or tetracoordinate nickel compound (II) which has at least one labile ligand and all ligands are neutral, an acid of the formula HX (IV), and a compound selected from the group consisting of:

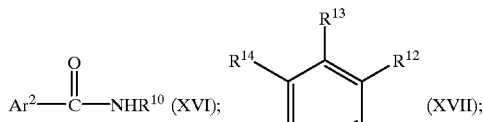

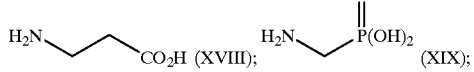

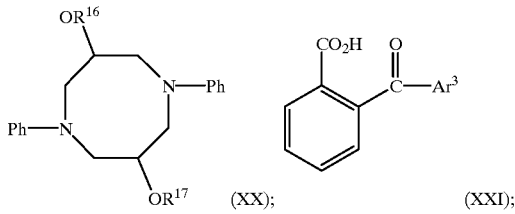

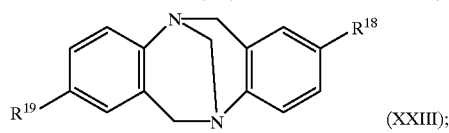

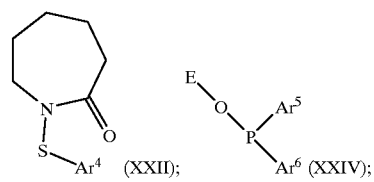

-continued

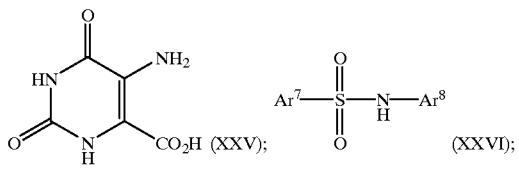

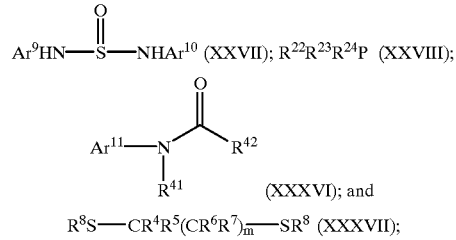

wherein:

X is a noncoordinating anion;

$Ar^1$ is an aromatic moiety with n free valencies, or diphenylmethyl;

each Q is —$NR^2R^{43}$ or —$CR^9$=$NR^3$;

n is 1 or 2;

E is 2-thienyl or 2-furyl;

$R^{43}$ is hydrogen or alkyl;

each $R^2$ is independently hydrogen, benzyl, substituted benzyl, phenyl or substituted phenyl;

each $R^3$ is independently a monovalent aromatic moiety;

each $R^9$ is independently hydrogen or hydrocarbyl;

m is 1, 2 or 3;

each $R^4$, $R^5$, $R^6$, and $R^7$ is independently hydrogen, hydrocarbyl or substituted hydrocarbyl;

each $R^8$ is independently hydrocarbyl or substituted hydrocarbyl containing 2 or more carbon atoms;

each $R^{10}$ is independently hydrogen, hydrocarbyl or substituted hydrocarbyl;

$Ar^2$ is an aryl moiety;

$R^{12}$, $R^{13}$, and $R^{14}$ are each independently hydrogen, hydrocarbyl, substituted hydrocarbyl or an inert functional group;

$R^{11}$ and $R^{15}$ are each independently hydrocarbyl, substituted hydrocarbyl or an inert functional group whose $E_s$ is about −0.4 or less;

each $R^{16}$ and $R^{17}$ is independently hydrogen or acyl containing 1 to 20 carbon atoms;

$Ar^3$ is an aryl moiety;

$R^{18}$ and $R^{19}$ are each independently hydrogen or hydrocarbyl;

$Ar^4$ is an aryl moiety;

$Ar^5$ and $Ar^6$ are each independently hydrocarby;

$Ar^7$ and $Ar^8$ are each independently an aryl moiety;

$Ar^9$ and $Ar^{10}$ are each independently an aryl moiety, —$CO_2R^{25}$, or $Ar^7$ and $Ar^8$ taken together are a divalent aromatic moiety and wherein $R^{25}$ is alkyl containing 1 to 20 carbon atoms;

$Ar^{11}$ is an aryl moiety;

$R^{41}$ is hydrogen or hydrocarbyl;

$R^{42}$ is hydrocarbyl or —C(O)—$NR^{41}$—$Ar^{11}$;

$R^{44}$ is aryl;

$R^{22}$ and $R^{23}$ are each independently phenyl groups substituted by one or more alkoxy groups, each alkoxy group containing 1 to 20 carbon atoms; and $R^{24}$ is alkyl containing 1 to 20 carbon atoms, or an aryl moiety;

and provided that the molar ratio of (III), (V) (XVI), (XVII), (XVIII), (XIX), (XX), (XXI), (XXII), (XXIII), (XXIV), (XXV), (XXVI), (XXVII), (XXVIII), (XXXVI) or (XXXVII):(II) is about 0.5 to about 5, and the molar ratio of (IV):(II) is about 0.5 to about 10.

This invention also concerns a process for the polymerization of an olefin, comprising, contacting ethylene, a norbornene, or a styrene with a nickel [II] complex of a ligand selected from the group consisting of:

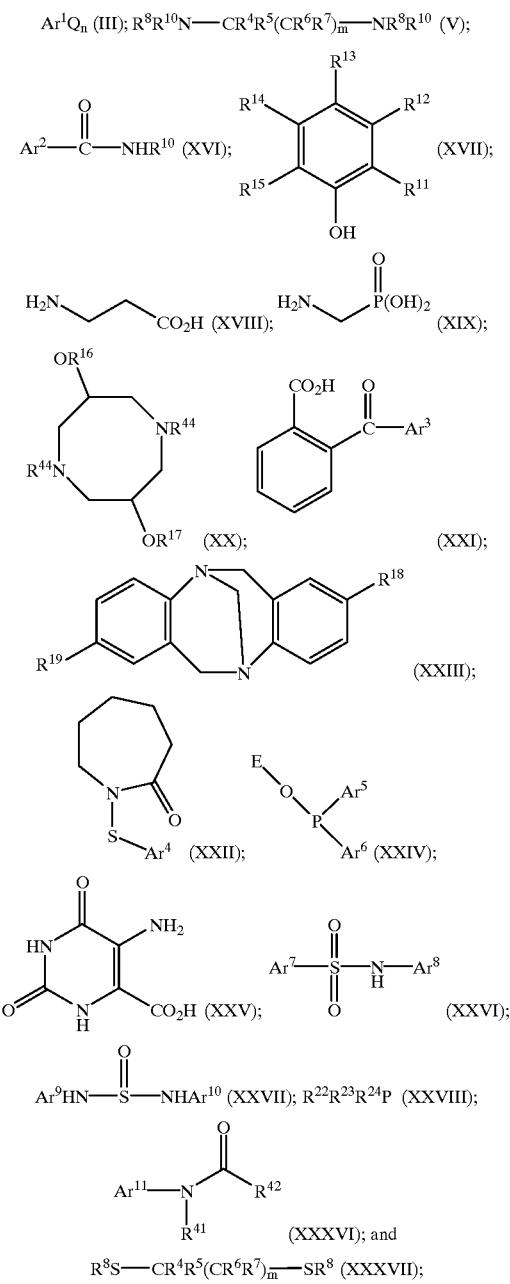

wherein:

X is a noncoordinating anion;

$Ar^1$ is an aromatic moiety with n free valencies, or diphenylmethyl;

each Q is $-NR^2R^{43}$ or $-CR^9=NR^3$;

$R^{43}$ is hydrogen or alkyl;

n is 1 or 2;

E is 2-thienyl or 2-furyl;

each $R^2$ is independently hydrogen, benzyl, substituted benzyl, phenyl or substituted phenyl;

each $R^3$ is independently a monovalent aromatic moiety;

each $R^9$ is independently hydrogen or hydrocarbyl; m is 1, 2 or 3;

each $R^4$, $R^5$, $R^6$, and $R^7$ is independently hydrogen, hydrocarbyl or substituted hydrocarbyl;

each $R^8$ is independently hydrocarbyl or substituted hydrocarbyl containing 2 or more carbon atoms;

each $R^{10}$ is independently hydrogen, hydrocarbyl or substituted hydrocarbyl;

$Ar^2$ is an aryl moiety;

$R^{12}$, $R^{13}$, and $R^{14}$ are each independently hydrogen, hydrocarbyl, substituted hydrocarbyl or an inert functional group;

$R^{11}$ and $R^{15}$ are each independently hydrocarbyl, substituted hydrocarbyl or an inert functional group whose $E_s$ is about −0.4 or less;

each $R^{16}$ and $R^{17}$ is independently hydrogen or acyl containing 1 to 20 carbon atoms;

$Ar^3$ is an aryl moiety;

$R^{18}$ and $R^{19}$ are each independently hydrogen or hydrocarbyl;

$Ar^4$ is an aryl moiety;

$Ar^5$ and $Ar^6$ are each independently hydrocarby;

$Ar^7$ and $Ar^8$ are each independently an aryl moiety;

$Ar^9$ and $Ar^{10}$ are each independently an aryl moiety, $-CO_2R^{25}$, or $Ar^7$ and $Ar^8$ taken together are a divalent aromatic moiety and wherein $R^{25}$ is alkyl containing 1 to 20 carbon atoms;

$Ar^{11}$ is an aryl moiety;

$R^{41}$ is hydrogen or hydrocarbyl;

$R^{42}$ is hydrocarbyl or $-C(O)-NR^{41}-Ar^{11}$;

$R^{44}$ is aryl;

$R^{22}$ and $R^{23}$ are each independently phenyl groups substituted by one or more alkoxy groups, each alkoxy group containing 1 to 20 carbon atoms; and $R^{24}$ is alkyl containing 1 to 20 carbon atoms, or an aryl moiety.

Described herein is a process for the polymerization of olefins, comprising, contacting ethylene, a norbornene or a styrene with a nickel containing first compound of the formula $[L^1_qL^2_rL^3_sL^4_tNi]^+X^-$ (XXXIII), wherein:

$L^1$ is a first monodentate neutral ligand coordinated to said nickel, $L^2$ is a second monodentate neutral ligand coordinated to said nickel which may be said first monodentate neutral ligand and r is 0 or 1, or $L^1$ and $L^2$ taken together are a first bidentate neutral ligand coordinated to said nickel and r is 1;

$L^3$ and $L^4$ taken together are a π-allyl ligand coordinated to said nickel, $L^3$ and $L^4$ taken together are

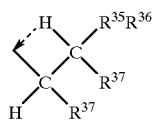
(XXXII)

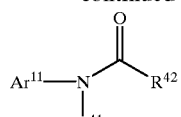
(XXXVI); and $R^8S\!-\!\!-\!CR^4R^5(CR^6R^7)_{\overline{m}}\!\!-\!SR^8$ (XXXVII);

coordinated to said nickel, or $L^3$ is a third neutral monodentate ligand selected from the group consisting of ethylene, a norbornene and a styrene or a neutral monodentate ligand which can be displaced by an olefin, and $L^4$ is $R^{38}$;

X is a relatively non-coordinating anion;

each of q, s and t is 1;

said first monodentate neutral ligand and said first bidentate neutral ligand are selected from the group consisting of $Ar^1Q_n$ (III); $R^8R^{10}N\!-\!CR^4R^5(CR^6R^7)_{\overline{m}}\!-\!NR^8R^{10}$ (V);

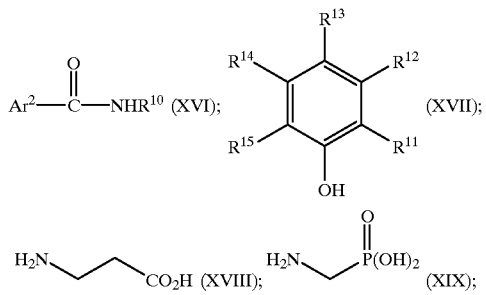

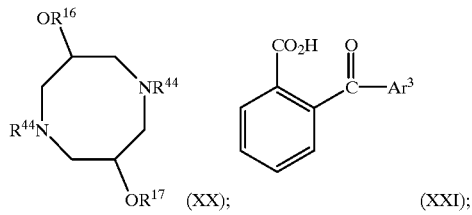

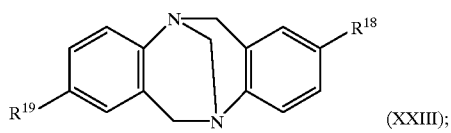

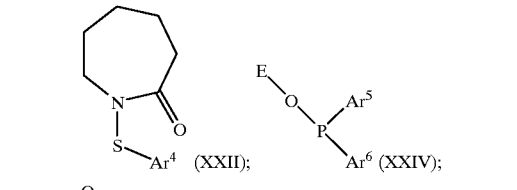

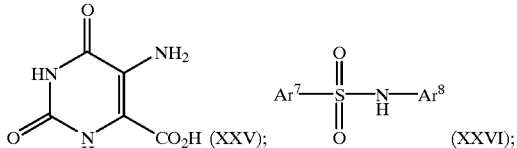

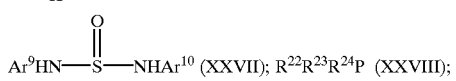

$Ar^9HN\!-\!\overset{\text{O}}{\underset{\text{S}}{\|}}\!-\!NHAr^{10}$ (XXVII); $R^{22}R^{23}R^{24}P$ (XXVIII);

$Ar^1$ is an aromatic moiety with n free valencies, or diphenylmethyl;
each Q is $-NR^2R^{43}$ or $-CR^9\!=\!NR^3$;
$R^{43}$ is hydrogen or alkyl;
n is 1 or 2;
E is 2-thienyl or 2-furyl;
each $R^2$ is independently hydrogen, benzyl, substituted benzyl, phenyl or substituted phenyl;
each $R^9$ independently hydrogen or hydrocarbyl; and
each $R^3$ is independently a monovalent aromatic moiety;
m is 1, 2 or 3;
each $R^4$, $R^5$, $R^6$, and $R^7$ is independently hydrogen, hydrocarbyl or substituted hydrocarbyl;
each $R^8$ is independently hydrocarbyl or substituted hydrocarbyl containing 2 or more carbon atoms;
each $R^{10}$ is independently hydrogen, hydrocarbyl or substituted hydrocarbyl;
$Ar^2$ is an aryl moiety;
$R^{12}$, $R^{13}$, and $R^{14}$ are each independently hydrogen, hydrocarbyl, substituted hydrocarbyl or an inert functional group;
$R^{11}$ and $R^{15}$ are each independently hydrocarbyl, substituted hydrocarbyl or an inert functional group whose $E_s$ is about -0.4 or less;
each $R^{16}$ and $R^{17}$ is independently hydrogen or acyl containing 1 to 20 carbon atoms;
$Ar^3$ is an aryl moiety;
$R^{18}$ and $R^{19}$ are each independently hydrogen or hydrocarbyl;
$Ar^4$ is an aryl moiety;
$Ar^5$ and $Ar^6$ are each independently hydrocarby;
$Ar^7$ and $Ar^8$ are each independently an aryl moiety;
$Ar^9$ and $Ar^{10}$ are each independently an aryl moiety or $-CO_2R^{25}$, wherein $R^{25}$ is alkyl containing 1 to 20 carbon atoms;
$Ar^{11}$ is an aryl moiety;
$R^{41}$ is hydrogen or hydrocarbyl;
$R^{42}$ is hydrocarbyl or $-C(O)-NR^{41}-Ar^{11}$;
$R^{22}$ and $R^{23}$ are each independently phenyl groups substituted by one or more alkoxy groups, each alkoxy group containing 1 to 20 carbon atoms; and
$R^{24}$ is alkyl containing 1 to 20 carbon atoms, or an aryl moiety;
$R^{35}$ is hydrocarbylene;
$R^{36}$ is hydrogen, alkyl, or $-C(O)$ $R^{39}$;
each $R^{37}$ is hydrocarbyl or both of $R^{37}$ taken together are hydrocarbylene to form a carbocyclic ring;
$R^{38}$ is hydride, alkyl or $-C(O)R^{39}$; and
$R^{39}$ is hydrocarbyl
$R^{44}$ is aryl.

Also described herein is a compound of the formula $[L^1{}_qL^2L^3{}_sL^4{}_tNi]^+X^-$ (XXXIII), wherein:
$L^1$ is a first monodentate neutral ligand coordinated to said nickel, $L^2$ is a second monodentate neutral ligand coordinated to said nickel which may be said first monodentate neutral ligand and r is 0 or 1, or $L^1$ and $L^2$ taken together are a first bidentate neutral ligand coordinated to said nickel and r is 1;

$L^3$ and $L^4$ taken together are a π-allyl ligand coordinated to said nickel, $L^3$ and $L^4$ taken together are

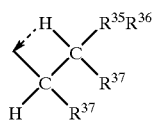

(XXXII)

coordinated to said nickel, or $L^3$ is a third neutral monodentate ligand selected from the group consisting of ethylene, a norbornene and a styrene or a neutral monodentate ligand which can be displaced by an olefin, and $L^4$ is $R^{38}$;

X is a relatively non-coordinating anion;

q, s and t are each 1;

said first monodentate neutral ligand and said first bidentate neutral ligand are selected from the group consisting of

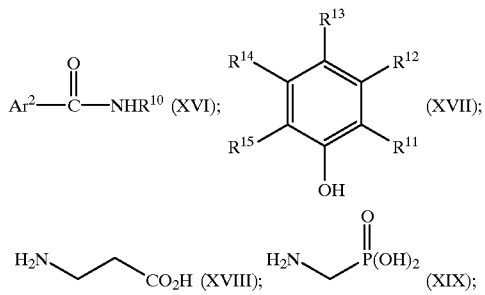

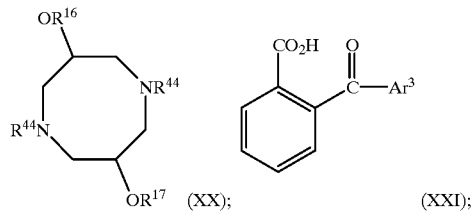

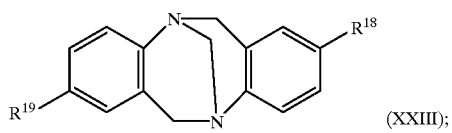

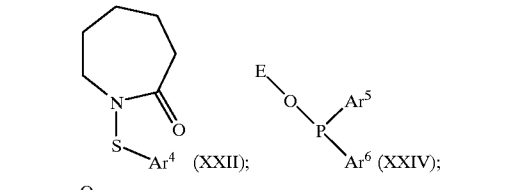

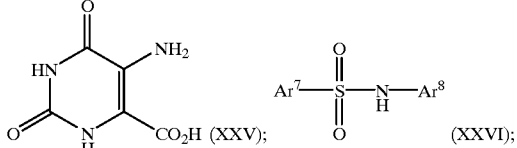

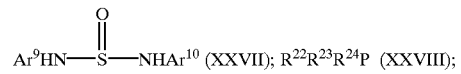

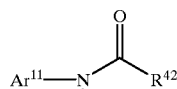

(XXXVI); and $R^8S$—$CR^4R^5(CR^6R^7)_{\overline{m}}$—$SR^8$ (XXXVII);

wherein:

$Ar^1$ is an aromatic moiety with n free valencies, or diphenylmethyl;

each Q is —$NR^2R^{43}$ or —$CR^9$=$NR^3$;

$R^{43}$ is hydrogen or alkyl;

n is 1 or 2;

E is 2-thienyl or 2-furyl;

each $R^2$ is independently hydrogen, benzyl, substituted benzyl, phenyl or substituted phenyl;

each $R^9$ is independently hydrogen or hydrocarbyl; and each $R^3$ is independently a monovalent aromatic moiety;

m is 1, 2 or 3;

each $R^4$, $R^5$, $R^6$, and $R^7$ is independently hydrogen, hydrocarbyl or substituted hydrocarbyl;

each $R^8$ is independently hydrocarbyl or substituted hydrocarbyl containing 2 or more carbon atoms;

each $R^{10}$ is independently hydrogen, hydrocarbyl or substituted hydrocarbyl;

$Ar^2$ is an aryl moiety;

$R^{12}$, $R^{13}$, and $R^{14}$ are each independently hydrogen, hydrocarbyl, substituted hydrocarbyl or an inert functional group;

$R^{11}$ and $R^{13}$ are each independently hydrocarbyl, substituted hydrocarbyl or an inert functional group whose $E_s$ is about −0.4 or less;

each $R^{16}$ and $R^{17}$ is independently hydrogen or acyl containing 1 to 20 carbon atoms;

$Ar^3$ is an aryl moiety;

$R^{18}$ and $R^{19}$ are each independently hydrogen or hydrocarbyl;

$Ar^4$ is an aryl moiety;

$Ar^5$ and $Ar^6$ are each independently hydrocarby;

$Ar^7$ and $Ar^8$ are each independently an aryl moiety;

$Ar^9$ and $Ar^{10}$ are each independently an aryl moiety or —$CO_2R^{25}$, wherein $R^{25}$ is alkyl containing 1 to 20 carbon atoms;

$Ar^{11}$ is an aryl moiety;

$R^{41}$ is hydrogen or hydrocarbyl;

$R^{42}$ is hydrocarbyl or —C(O)—$NR^{41}$—$Ar^{11}$;

$R^{44}$ is aryl;

$R^{22}$ and $R^{23}$ are each independently phenyl groups substituted by one or more alkoxy groups, each alkoxy group containing 1 to 20 carbon atoms; and $R^{24}$ is alkyl containing 1 to 20 carbon atoms, or an aryl moiety;

$R^{35}$ is hydrocarbylene;

$R^{36}$ is hydrogen, alkyl, or —C(O)$R^{39}$;

each $R^{37}$ is hydrocarbyl or both of $R^{37}$ taken together are hydrocarbylene to form a carbocyclic ring;

$R^{38}$ is hydride, alkyl or —C(O)$R^{39}$; and $R^{39}$ is hydrocarbyl.

Described herein is a compound of the formula

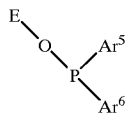

(XXIV)

wherein:
E is 2-thienyl or 2-furyl;
$Ar^5$ and $Ar^6$ are each independently hydrocarby.

DETAILS OF THE INVENTION

The olefins polymerized herein are ethylene, a styrene and a norbornene. Norbornene and styrene may be present in the same polymerization, and a copolymer may be produced. By a styrene herein is meant a compound of the formula

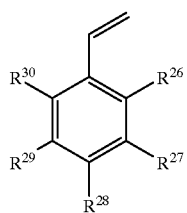

(XXIX)

wherein $R^{26}$, $R^{27}$, $R^{26}$, $R^{29}$ and $R^{30}$ are each independently hydrogen, hydrocarbyl, substituted hydrocarbyl or a functional group, all of which are inert in the polymerization process. It is preferred that all of $R^{26}$, $R^{27}$, $R^{26}$, $R^{29}$ and $R^{30}$ are hydrogen.

By "a norbornene" is meant that the monomer is characterized by containing at least one norbornene-functional group in its structure including norbornadiene as identified by the formulas below, which can be substituted or unsubstituted

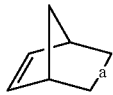

(XXXIV)

wherein "a" represents a single or double bond.

Representative monomers are compounds (XXXV) and (XXXX) as follows:

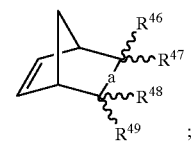

(XXXIV)

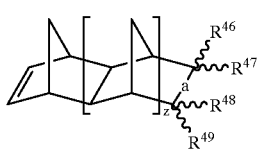

(XXXX)

wherein $R^{46}$, $R^{47}$, $R^{48}$, and $R^{49}$ independently are hydrogen halogen, or hydrocarbyl, provided that, except if the hydrocarbyl group is vinyl, if any of the hydrocarbyl are alkenyl, there is no terminal double bond, i.e., the double bond is internal; or $R^{46}$ and $R^{48}$ taken together can be part of carbocyclic ring (saturated, unsaturated or aromatic); or $R^{46}$ and $R^{47}$ and/or $R^{48}$ and $R^{49}$ taken together are an alkylidene group. In these structures "z" is 1 to 5.

Examples of such norbornenes include norbornadiene, 2-norbornene, 5-methyl-2-norbornene, 5-hexyl-2-norbornene, 5-ethylidene-2-norbornene, vinylnorbornene, dicyclopentadiene, dihydrodicyclopentadiene, tetracyclododecene, trimers of cyclopentadiene, halogenated norbornenes wherein $R^{46}$, $R^{47}$, $R^{48}$ and $R^{49}$ may also be halogen or fully halogenated alkyl groups such as $C_wF_{2w+1}$ wherein w is 1 to 20, such as perfluoromethyl and perfluorodecyl.

The halogenated norbornenes can be synthesized via the Diels-Alder reaction of cyclopentadiene an appropriate dieneophile, such as $F_3CC\equiv CCF_3$ or $R^{49}{}_2C=CR^{49}C_wF_{2w+1}$ wherein each $R^{49}$ is independently hydrogen or fluorine and w is 1 to 20.

It is also preferred that in the polymerization processes described herein that the polymer produced has an average degree of polymerization of about 10 or more, more preferably about 20 or more, and especially preferably about 50 or more.

In the polymerization processes and catalyst compositions described herein certain groups may be present. By hydrocarbyl is meant a univalent radical containing only carbon and hydrogen. By saturated hydrocarbyl is meant a univalent radical which contains only carbon and hydrogen, and contains no carbon-carbon double bonds, triple bonds and aromatic groups. By substituted hydrocarbyl herein is meant a hydrocarbyl group which contains one or more (types of) substitutents that does not interfere with the operation of the polymerization catalyst system. Suitable substituents include halo, ester, keto (oxo), amino, imino, carboxyl, phosphite, phosphonite, phosphine, phosphinite, thioether, amide, nitrile, and ether. Preferred substituents are halo, ester, amino, imino, carboxyl, phosphite, phosphonite, phosphine, phosphinite, thioether, and amide. By benzyl is meant the $C_6H_5CH_2$— radical, and substituted benzyl is a radical in which one or more of the hydrogen atoms is replaced by a substituent group (which may include hydrocarbyl). By phenyl is meant the $C_6H_5$— radical, and a phenyl moiety or substituted phenyl is a radical in which one or more of the hydrogen atoms is replaced by a substituent group (which may include hydrocarbyl). Preferred substituents for substituted benzyl and phenyl include those listed above for substituted hydrocarbyl, plus hydrocarbyl. If not otherwise stated, hydrocarbyl, substituted hydrocarbyl and all other groups containing carbon atoms, such as alkyl, preferably contain 1 to 20 carbon atoms.

By an aromatic moiety herein is meant a radical containing at least one carbocyclic or heterocyclic aromatic ring, which has a number of free valences to the carbon atoms of the aromatic carbocyclic ring(s). A monovalent aromatic moiety has one free valence, and herein is termed an aryl moiety. If there is more than one aromatic ring in the radical, the ring may be joined by covalent bonds (as in biphenyl) or may be fused (as in naphthalene), or both. The free valencies may be at carbon atoms in one ring, or more than one ring if more than one ring is present. The aromatic ring(s) may be substituted by hydrocarbyl groups or other substitutents which don't interfere with the catalytic activity of the catalyst system. Substituents that aid the polymerization may be present. Suitable and preferred substituents are as listed above for substituted hydrocarbyl groups. Suitable aromatic radicals herein include phenyl, o-phenylene, 1,8-naphthylene, and 2-thiophenyl.

A transition metal compound which may be initially added to a polymerization process mixture is (II), a zerovalent nickel compound which is tricoordinate or tetracoordinate. Also included within the definition of this zerovalent nickel compound are mixtures of compounds which will generate suitable zerovalent nickel compounds in situ, such as mixtures of nickel compounds in higher valence states with suitable reducing agents. The ligands which are coordinated to the nickel atom may be monodentate or polydentate, so long as the nickel compound is tricoordinate or tetracoordinate. The ligands should be such that at least two, and preferably all, of the coordination sites of the nickel atom are coordinated to ligands which are readily, reversibly or irreversibly, displaceable by (III),(V), or any one of (XVI) to (XIX), (XXXVI) and (XXXVII). Such readily displaceable ligands include $\eta^4$-1,5-cyclooctadiene and tris(o-tolyl)phosphite (which is a phosphite with a large cone angle), ethylene and carbon monoxide. A preferred nickel compound (II) is bis($\eta^4$-1,5-cyclooctadiene)nickel[0].

By the compound HX is meant the acid of a noncoordinating monoanion, or the equivalent thereof, i.e., a combination of compounds that will generate this acid. Noncoordinating anions are well known to the artisan, see for instance W. Beck., et al., Chem. Rev., vol. 88, p. 1405–1421 (1988), and S. H. Strauss, Chem. Rev., vol. 93, p. 927–942 (1993), both of which are hereby included by reference. Relative coordinating abilities of such noncoordinating anions are described in these references, Beck at p. 1411, and Strauss at p. 932, Table III. Also useful in this process in place of HX are "solid" acids, such as acidic aluminas, clays and zirconias, which are considered herein to be acids with relatively non-coordinating anions.

Preferred anions X are $BF_4^-$, $PF_6^-$, and BAF {tetrakis[3,5-bis(trifluoromethyl)phenyl]borate}, $SbF^-$, and BAF is especially preferred. The acids of these anions are known, for instance $HBF_4$ is commercially available, and HBAF can be made by the method described in M. Brookhart, et al., Organometallics, vol. 11, p. 3920–3922 (1992).

In all forms of (III) it is preferred that $R^9$ and $R^{43}$ are hydrogen. If $R^{43}$ is alkyl, it is preferred that it is methyl. In all forms of (III), each $R^2$ may be independently hydrogen, hydrocarbyl or substituted hydrocarbyl, and it is preferred that each $R^2$ is hydrogen, benzyl, substituted benzyl, phenyl or substituted phenyl.

In one preferred form of (III), n is 1 and Q is $-NR^2R^{43}$. It is preferred that $R^2$ is hydrogen and that $Ar^1$ is 2,6-dialkylphenyl or amide, carboxy, or keto substituted phenyl. More preferably, $Ar^1$ is 2,6-diisopropylphenyl, 2-carbomoylphenyl, 2-carboxyphenyl, or 2-benzoylphenyl.

In another preferred form of (III), n is 2 and each Q is $-NR^2R^{43}$. In this instance it is more preferred that $R^2$ is hydrogen, and/or $Ar^1$ is o-phenylene or 1,8-naphthylene, and it is especially preferred that $Ar^1$ is 1,8-naphthylene.

In (III), when n is 1 and Q is $-CR^9=NR^3$, it is preferred that $R^9$ is hydrogen, and $R^3$ is preferably 2,6-dialkylphenyl, or amide, ester, carboxyl, keto, or halo substituted phenyl. More preferably, $R^3$ is 2,6-diisopropylphenyl, 2-carbomoylphenyl, 2-carbomethoxyphenyl, 2-carboxyphenyl, 1-fluoren-9-onyl, 1-anthraquinolyl, or pentafluorophenyl. $Ar^1$ is aryl, or halo, ester, amino, imino, carboxyl, phosphite, phosphonite, phosphine, phosphinite, ether, thioether, or amide substituted phenyl. More preferably, $Ar^1$ is diphenylmethyl, 9-anthracenyl, 2-furanyl, 2-thiofuranyl, 2-phenolyl, or 2-hydroxy-naphthyl. When $Ar^1$ is diphenylmethyl, these tautomeric forms are believed to exist when these compounds are complexed to nickel.

When in (III) n is 2 and Q is $-CR^9=NR^3$, it is preferred that $Ar^1$ is p-phenylene, and that $R^3$ is 2,6-disubstituted phenyl in which the substitutents are halo, alkyl, or halo and alkyl.

In (III), when Q is $-NHR^2$, $R^2$ taken together with $Ar^1$ may form a carbocyclic or heterocyclic ring, as long as the atom of $R^2$ attached directly to the nitrogen atom is a saturated carbon atom. Thus another preferred compound (III) is

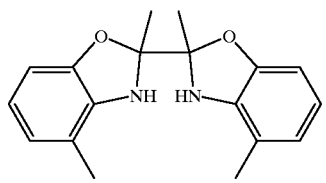

It will be noted that there are actually two amino groups in this compound that meet the criteria for Q. This is compound 105, below.

For (V) it is preferred that m is 1, all of $R^4$, $R^5$, $R^6$, $R^7$ and $R^{10}$ are hydrogen, and both of $R^8$ are 2,6-dialkylphenyl, especially 2,6-diisopropylphenyl, or cyclohexyl. In another preferred compound (V) m is 1, all of $R^4$, $R^5$, $R^6$, and $R^7$ are hydrogen, both of $R^8$ are phenyl, and both of $R^{10}$ are ethyl. In (V) too much or too little steric hindrance around the nitrogen atoms may cause a catalytic composition containing such a compound to be ineffective as an olefin polymerization catalyst.

In (XVI) is preferred that $Ar^2$ is phenyl, 2-pyridyl, or 3-hydroxyl-2-pyridyl, and/or $R^{10}$ is hydrogen, phenyl, 2,6-diisopropylphenyl,1-naphthyl, 2-methyl-1-naphthyl, or 2-phenylphenyl.

In (XVII) it is preferred that $R^{12}$ and $R^{14}$ are hydrogen, and/or $R^{13}$ is hydrogen or t-butyl, and/or $R^{11}$ and $R^{15}$ are both t-butyl or both phenyl, and/or $R^{11}$ is t-butyl and $R^{15}$ is 2-hydroxy-3,5-di-t-butylphenyl. Note that when $R^{15}$ is 2-hydroxy-3,5-di-t-butylphenyl the compound contains 2 phenolic hydroxy groups, both of which are sterically hindered.

The steric effect of various groupings has been quantified by a parameter called $E_s$, see R. W. Taft, Jr., J. Am. Chem. Soc., vol. 74, p. 3120–3128 (1952), and M. S. Newman, Steric Effects in Organic Chemistry, John Wiley & Sons, New York, 1956, p. 598–603. For the purposes herein, the $E_s$ values are those described in these publications. If the value for $E_s$ for any particular group is not known, it can be determined by methods described in these publications. For the purposes herein, the value of hydrogen is defined to be the same as for methyl. It is preferred that the total $E_s$ value for the ortho (or other substituents closely adjacent to the $-OH$ group) substitutents in the ring be about −1.5 or less, more preferably about −3.0 or less. Thus in a compound such as 2,4,6-tri-t-butylphenol only the $E_s$ values for the 2 and 6 substituted t-butyl groups would be applicable.

In (XX) it is preferred that both $R^{16}$ and $R^{17}$ are hydrogen or that both are acyl. A preferred acyl group is $CH_3C(O)-$.

In (XXI) it is preferred that $Ar^3$ is phenyl or substituted phenyl, more preferably phenyl.

In (XXII) it is preferred that both of $R^{18}$ and $R^{19}$ are methyl, or both are hydrogen.

In (XXIII) it is preferred that $Ar^4$ is phenyl or substituted phenyl, more preferably phenyl.

In (XXIV) it is preferred that $Ar^5$ and $Ar^6$ are independently phenyl, substituted phenyl, or cyclohexyl, and it is especially preferred when both are cyclohexyl or both are phenyl.

In (XXVI) it is preferred that $Ar^7$ and $Ar^8$ are independently phenyl or substituted phenyl. In a specific preferred compound, $Ar^7$ is phenyl or p-tolyl and $Ar^8$ is 2,6-diisopropylphenyl.

In (XXVII) it is preferred that $R^{25}$ is methyl. Specific preferred compounds are

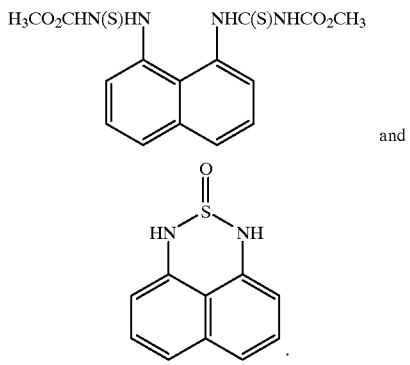

and

Note that in one of these compounds there are 2 thiourea groups present.

In (XXVIII) it is preferred that $R^{22}$, $R^{23}$ and $R^{24}$ are each independently o-tolyl, 2,4,6-trimethoxyphenyl, 2,6-dimethoxyphenyl, 2-methoxyphenyl, and 2,3,6-trimethoxyphenyl. Other preferred groups for $R^{24}$ are ethyl, isopropyl and phenyl. It is also preferred that $R^{24}$ is an aryl moiety. In another preferred form, when $R^{22}$, $R^{23}$ and/or $R^{24}$ are phenyl or substituted phenyl, there is at least one alkoxy group, preferably a methoxy group, ortho (in the benzene ring) to the phosphorous atom. Another compound (XXVIII) is 1,3-bis[(bis-2,6-dimethoxyphenyl)phosphino]propane. This compound actually has two phosphine groups that each structurally meet the requirements for a compound of type (XXVIII).

It is also preferred that each of $R^{22}$, $R^{23}$, and $R^{24}$ (when it is an aryl moiety) contain electron donating groups bound to the aromatic moiety through a carbon atom of an aromatic ring. The concept of electron donating groups is well known to the artisan. One method of measuring the electron donating ability of a group (particularly in a benzene ring, but it is not limited to such rings) which is not adjacent to the "active" center is by using the Hammett equation, see for instance H. H. Jaffe, Chem. Rev., vol. 53, p. 191–261 (1953). The actual result of this is called the Hammett σ constant. For ortho (adjacent) substituents one may use the Taft σ* constant as determined by measurements on orthobenzoate esters, see for instance R. W. Taft, Jr., J. Am. Chem. Soc., vol. 74, p. 3120–3128 (1952); ibid., vol. 75, p. 4231–4238 (1953); and C. K. Ingold, Structure and Mechanism in Organic Chemistry, 2nd Ed., Cornell University Press, Ithaca, 1969, p. 1220–1226. It is preferred that the total of the σ and σ* constants for any of the groups $R^{22}$, $R^{23}$, and $R^{24}$ (when it is an aryl moiety) be about −0.25 or less, more preferably about −0.50 or less (it is noted that the σ and σ* constants for electron donating groups are negative, so the more electron donating groups present, the more negative this total becomes) and especially preferably about −0.75 or less.

In (XXXVI) it is preferred that $Ar^{11}$ is 2,6-dialkylphenyl, more preferably 2,6-dimethylphenyl or 2,6-diisopropylphenyl. It is preferred that $R^{42}$ is —C(O)—$NR^{41}$—$Ar^{11}$. It is preferred that $R^{41}$ is hydrogen.

In (XXXVII) it is preferred that m is 1, and/or all of $R^4$, $R^5$, $R^6$ and $R^7$ are hydrogen, and/or both of $R^8$ are aryl moieties, more preferably both of $R^8$ are 2,6-dialkylphenyl, and especially preferably both of $R^8$ are 2,6-dimethylphenyl.

In some of the compounds herein, the group —$CHPh_2$, diphenylmethyl, may appear, especially when the methine carbon atom can be bound to the carbon atom of an imine. In this case one can write such a compound as —N=CH—$CHPh_2$ (the imine form) or as —NH—CH=$CPh_2$ (amine form). It has been found that in the free compounds (not complexed to nickel) this group is usually in the amine form. However, in a few of the nickel complexes of these types of compounds the preliminary evidence indicates the ligand is present in the imine form. Therefore, one may consider these forms interchangeable for the purposes herein, and it is noted that both types of compounds are mentioned in the claims herein.

The ligands can be made by methods that can be readily found in the literature, and/or are available commercially or form laboratory supply houses, or are described in the Examples herein.

The polymerization may also be carried out by $[L^1_q L^2_r L^3_s L^4_t Ni]^+ X^-$ (XXXIII), which may be formed in situ or added directly to the initial polymerization mixture. For example, (XXXIII) may be in the form of a π-allyl complex. By a π-allyl group is meant a monoanionic radical with 3 adjacent $sp^2$ carbon atoms bound to a metal center in an $\eta^3$ fashion. The three $sp^2$ carbon atoms may be substituted with other hydrocarbyl groups or functional groups. Typical π-allyl groups include

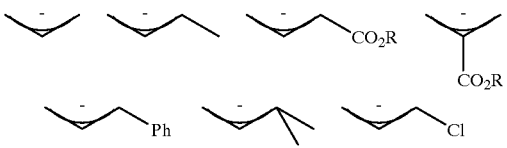

wherein R is hydrocarbyl. In (XXXIII) when it is a π-allyl type complex, $L^3$ and $L^4$ taken together are the π-allyl group. As shown in many of the Examples herein, these π-allyl compounds may be stable, and may be used themselves to initiate the olefin polymerization.

Initiation with π-allyl compounds may be sluggish at times. Initiation of π-allyl compounds can be improved by using one or more of the following methods:

Using a higher temperature such as about 80° C.

Decreasing the bulk of the ligand, such as $R^2$ and $R^5$ being 2,6-dimethylphenyl instead of 2,6-diisopropylphenyl.

Making the π-allyl ligand more bulky, such as using

rather than the simple π-allyl group itself.

Having a Lewis acid present while using a functional π-allyl. Relatively weak Lewis acids such a triphenylborane, tris(pentafluorophenyl)borane, and tris(3,5-trifluoromethylphenyl)borane, are preferred. Suitable functional groups include chloro and ester. "Solid" acids such as montmorillonite may also be used.

However, (XXXIII) may also be present in the polymerization in other "forms". For instance, $L^3$ may be an olefin, such as ethylene, a norbornene or a styrene or a ligand capable of being displaced by an olefin. By a ligand capable of being displaced by an olefin is meant that the ligand is more weakly coordinating to nickel than an olefin, and when in the complex is in contact with an olefin, the olefin displaces it. Such ligands are known in the art and include dialkyl ethers, tetrahydrofuran and nitriles such as acetonitrile.

When $L^3$ is an olefin, $L^4$ may be $-R^{35}R^{36}$. $R^{35}$ is alkylene, but it actually is a "polymeric" fragment with one or more repeat units (derived from the olefin(s) being polymerized) making up $R^{35}$. In this form (XXXIII) may be said to be a living ended polymer, further polymerization adding more repeat units to $R^{35}$. $R^{36}$ may be thought of as the end group of the polymeric group $R^{35}$, and may be derived from the similar grouping such as $R^{38}$ which was originally coordinated to the nickel.

When $L^3$ and $L^4$ in (XXXIII) taken together are (XXXII), (XXXIII) may also be thought of as a living polymer. This type of grouping is often referred to as an "agostic" coordination, and in this group $-R^{35}R^{36}$ may be thought of in the same way as described above. Whether a living ended molecule will be in a form with a coordinated olefin or contain (XXXII) will depend on the other ligands coordinated to nickel, and the nature of the olefin being polymerized. It is believed that cyclic olefins tend to have living ends containing agostic groupings.

In (XXXIII) it is preferred that r is 1. The second monodentate neutral ligand may be any ligand which fits this description, including being the same as the first neutral monodentate ligand. Oftentimes though this ligand is a dialkyl ether such as diethyl ether or an aliphatic nitrile such as acetonitrile, or tetrahydrofuran. By "neutral" in the context of (XXXIII) is meant that the ligand is electrically neutral, i.e., is not charged. In (XXXIII) preferred structures for the first neutral monodentate ligand are those shown above. However, in certain circumstances, $L^1$ and $L^2$ may be a single neutral bidentate ligand of the same formula as when $L^1$ is a neutral monodentate ligand. In other words, some of the compounds (III), (V), (XVI) to (XXVIII), (XXXVI) and (XXXVII) may act as bidentate ligands in (XXXIII). This may depend on the ligand itself, what the ratio of ligand to Ni is, what the other ligands may be, and whether there are any other compounds present which may also act as ligands.

When r in (XXXIII) is zero, simple dimers (containing 2 Ni atoms) with bridging ligands of the compound $[L^1L^3L^4Ni]^+X^-$ are also included within the definition of (XXXIII). For instance a dimer containing $L^1$, r is zero, and $L^3$ and $L^4$ are combined into an π-allyl group could have the formula

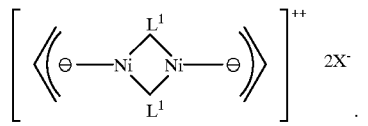

In this structure both $L^1$ ligands are bridging between the 2 nickel atoms. This type of dimer is familiar to those skilled in the art, and is believed to readily disassociate into "monomeric" nickel compounds on exposure to olefin.

Some of the forms of (XXXIII) are relatively unstable, and are difficult to isolate as pure compounds. Nevertheless their presence can be demonstrated by various methods known in the art. For instance, "living end" and other forms of (XXXIII) may be detected in solution by nuclear magnetic resonance (NMR) analysis, especially a combination of $^1$H and $^{13}$C NMR. Such detection of living ends is usually best done when $R^{35}$ contains relatively few repeat units.

(XXXIII) may be made by methods described herein, especially in the Examples, or may actually be formed in situ at the beginning of or during the polymerization process. It is believed that when (III), (V), (XVI) to (XXVIII), (XXXVI) or (XXXVII), and (II) and HX are mixed together in solution a coordination compound such as (XXXIII) is formed which is active as a catalyst for the polymerization of olefins.

The preparation of one of the catalyst systems, when (II) is used, may be carried out in solution. By solution is meant that (II) and (III), (V), (XVI) to (XIX), (XXXVI) or (XXXVII), and (IV) are at least initially somewhat soluble in the solvent chosen. By somewhat soluble is meant that at least a 0.01 molar solution of each of the components in the solvent may be formed under process conditions. This catalyst system may them be removed from the solvent, as by evaporation of the solvent under vacuum, and then contacted with one or more olefins to carry out the polymerization. However, it is preferred to carry out the polymerization in the presence of the "original" solvent in which the active catalyst is formed. One or more of the components, including the polymer product, may become insoluble as the polymerization proceeds. Useful solvents include hydrocarbons such as toluene or benzene. Benzene is a preferred solvent. The benzene used herein is benzene-$d_6$.

Although it is not critical, when (II) is present it is preferred that the molar ratio of (III), (V), (XVI) to (XXVIII), (XXXVI) or (XXXVII):(II) is about 0.5 to 5, and the molar ratio of (IV):(II) is about 0.5 to about 10. It is also preferred that all the polymerizations be carried out at a temperature of about −100° C. to about +200° C., more preferably about −20° C. to about +100° C.

The polymers produced by this process are useful as molding resins, films and elastomers.

Most of the formulas for (III), (V), (XVI) to (XXVIII), (XXXVI) and (XXXVII) are generic formulas and embrace a wide range of actual compounds. The ability of such individual compounds to form active polymerizations catalysts, and the actual activity of those catalysts, will be dependent on the structure of the individual compound used, and the circumstances under which it is used. For instance, whether such a compound will be active and how active it will be will be dependent to some extent on its actual structure, and particularly how that structure affects the steric and electronic properties of the compound as a ligand on nickel. If there is too much or too little steric hindrance about the group that actually coordinates to the nickel atom, the compound may be ineffective. Similarly, if the group that actually coordinates to the nickel is made too electron rich or poor, the compound may be made ineffective.

This may be illustrated by the following list of compounds, which were ineffective in catalyzing the polymerization of ethylene under the conditions described for Examples 23–66. The specific compounds are:

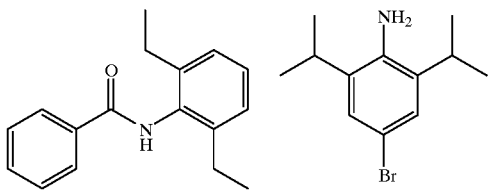

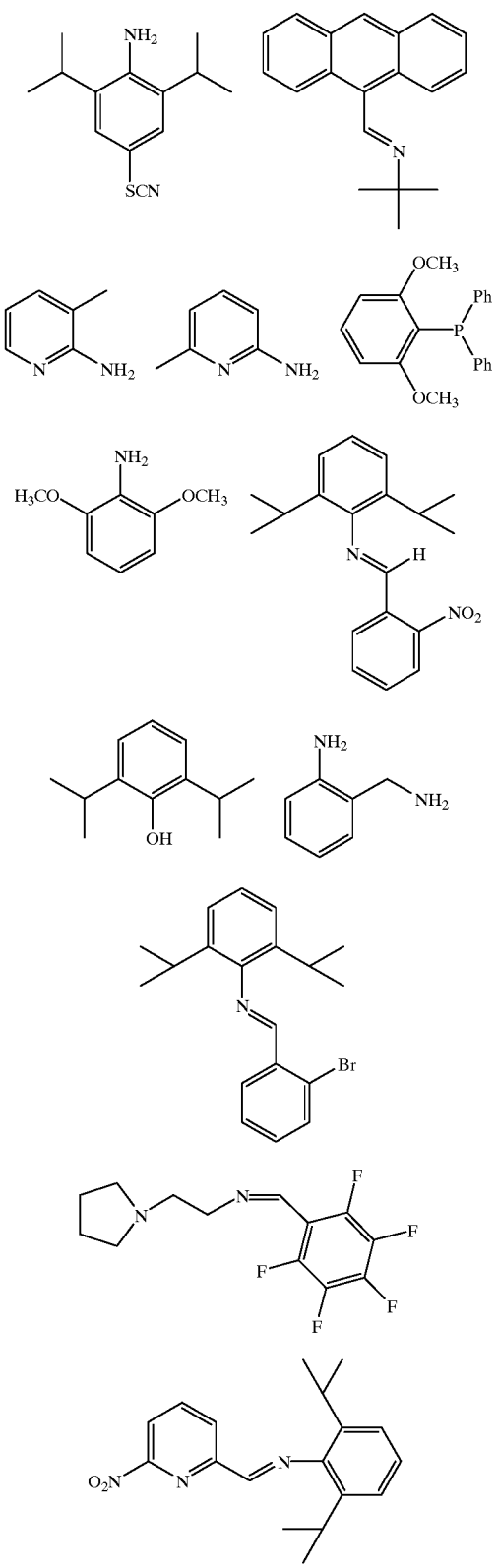

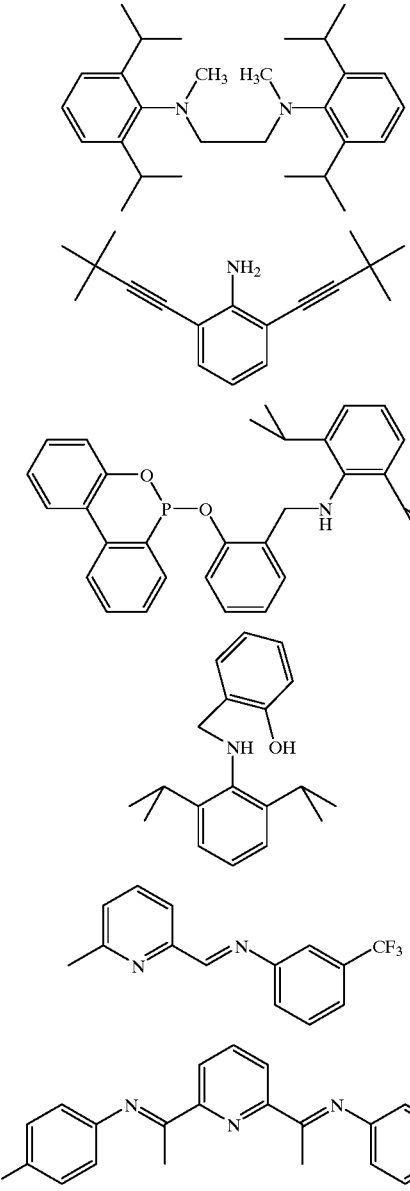

However, as mentioned above these compounds failed under a specific set of conditions. If one peruses through the Examples herein, one will find that certain of these compounds may fail to promote polymerization by one method, while be active in another method, and/or one finds the yield of polymer may change significantly under different conditions. Therefore failure in any particular polymerization process doesn't mean failure in all.

Conditions in such processes may be varied, for instance the pressure, temperature and solvent used. The polymerizations may be carried out in slurry, solution or the gas phase, in continuous, semi-batch or batch reactors. In addition, the particular starting form of the (proto)catalyst system may affect reactivity. For instance, differences may be found when using (II) as a starting material than when using a preformed π-allyl complex.

Determining the activity of any particular compound which is described herein is relatively easy. The compound may be used in any of the polymerization systems described herein, and if needed the conditions, such as temperature and pressure, may be varied. Particularly for polymerizations in which the active nickel catalyst is formed in situ, it may be important that the catalyst components all be soluble, at least initially, so solvent selection may be important. Such experiments are simple and quick to run and don't involve much experimentation.

It is also noted that some forms of (XXXIII) may be prepared by other methods known in the art, see for instance copending U.S. application Ser. No. 08/590,650, filed Jan. 24, 1996 (CR9608D) which is hereby included by reference.

In all of the polymerization processes and polymerization catalysts herein it is preferred that one or more of the following not be significantly present: an organoaluminum compound; an aluminum halide; any other transition metals, especially titanium and/or zirconium; reducing agents, especially metal or metalloid hydrides; and any organometalic compound except for nickel compounds. By not significantly present is meant there is not enough present to affect the course of the polymerization. It is more preferred that one or more of these be absent from a polymerization process and/or polymerization catalyst, except for normal impurities. It is also preferred that a polymerization catalyst or catalyst system for a polymerization process herein consist essentially of the stated ingredients.

In all of the nickel complexes herein, except those specifically enumerated as nickel [0] complexes, it is preferred that the nickel be in the +2 oxidation state.

In the Examples the following abbreviations are used:
BAF—{tetrakis[3,5-bis(trifluoromethyl)phenyl]borate}
Bu—butyl
COD—$\theta^4$-1,5-cyclooctadiene
Cy—cyclohexyl
DSC—differential scanning calorimetry
Et—ethyl
Me—methyl
Ph—phenyl ($C_6H_5$—)
RT—room temperature
Tg—glass transition temperature
THF—tetrahydrofuran
TLC—thin layer chromatography
Tm—melting point In the Examples, all ethylene pressures are gauge pressures unless otherwise noted. The formulas given for the nickel complexes of specific ligands in the Examples may not be accurate and are for illustration purposes only. They represent the best estimate of the structure (or one of several possible structures) based on available data.

EXAMPLE 1

Under a nitrogen atmosphere, Ni(COD)$_2$ (0.017 g, 0.06 mmol) and compound (VI) (0.023 g, 0.06 mmol) (purchased from the SALOR fine chemical division of Aldrich Chemical Co.) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was washed with methanol and dried; yield of polymer =9.1 g. $^1$H NMR (CDCl$_2$CDCl$_2$, 120° C.) showed that this sample contained 90 methyl-ended branches per 1000 methylenes. Two melting points were observed by differential scanning calorimetry: a very broad melting point centered at approximately 0° C., and a sharp melting point at 115° C.

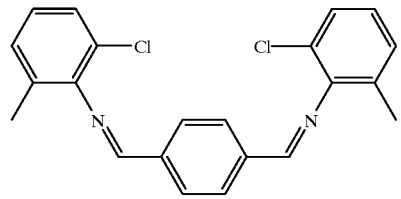

(VI)

EXAMPLE 2

Under a nitrogen atmosphere, Ni(COD)$_2$ (0.017 g, 0.06 mmol) and compound (VII) (0.023 g, 0.06 mmol) were dissolved in benzene (5.0 mL). To the resulting solution was added HBAF (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was filtered off, washed with methanol and dried; yield of polymer =4.9 g. By $^1$H NMR integration it was shown that this material was branched polyethylene containing 109 methyl-ended branches per 1000 methylenes. $^1$H NMR (CDCl$_3$) d 1.24 (s, methylene and methine protons), 0.82 (d, methyls).

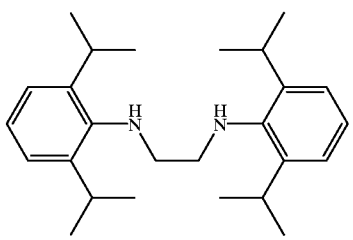

(VII)

EXAMPLE 3

Under a nitrogen atmosphere, Ni(COD)$_2$ (0.017 g, 0.06 mmol) and compound (VIII) (0.024 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was filtered off, washed with methanol and dried; yield of polymer =0.26 g. $^1$H NMR (C$_6$D$_3$Cl$_3$, 120° C.) showed that this sample contained 18 methyl-ended branches per 1000 methylenes.

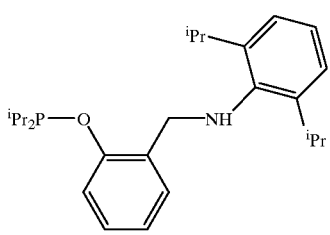

(VIII)

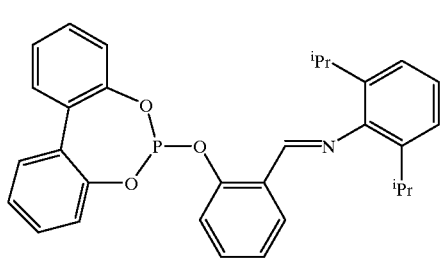

(X)

EXAMPLE 4

Under a nitrogen atmosphere, Ni(COD)$_2$ (0.017 g, 0.06 mmol) and compound (IX) (0.020 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was washed with methanol and dried; yield of polymer =0.73 g. T$_m$=126.9° C. (second heat) as determined by DSC. $^1$H NMR (CDCl$_2$CDCl$_2$, 25° C.) showed that this sample contained approximately 7 methyl-ended branches per 1000 methylenes.

EXAMPLE 6

Under a nitrogen atmosphere, Ni(COD)$_2$ (0.017 g, 0.06 mmol) and compound (XI) (0.029 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was filtered off, washed with methanol and dried; yield of polymer =0.43 g. $^1$H NMR (CDCl$_2$CDCl$_2$, 120° C.) showed that this sample contained 19 methyl-ended branches per 1000 methylenes.

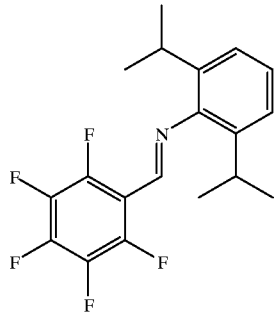

(IX)

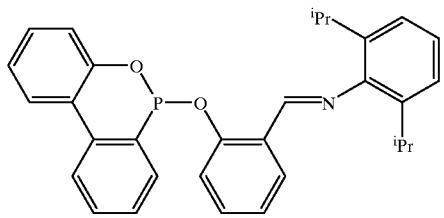

(XI)

EXAMPLE 5

Under a nitrogen atmosphere, Ni(COD)$_2$ (0.017 g, 0.06 mmol) and compound (X) (0.030 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was washed with methanol and dried; yield of polymer =1.40 g. T$_m$=123.6° C. as determined by DSC. $^1$H NMR (CDCl$_2$CDCl$_2$, 120° C.) showed that this sample contained approximately 10 methyl-ended branches per 1000 methylenes.

EXAMPLE 7

Under a nitrogen atmosphere, Ni(COD)$_2$ (0.017 g, 0.06 mmol) and 2,6-diisopropylaniline (0.011 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h at 25° C. The final reaction mixture contained polyethylene, which was filtered off, washed with methanol and dried; yield of polymer =0.72 g. T$_m$=121.3° C. (second heat) as determined by DSC. $^1$H NMR (C$_6$D$_3$Cl$_3$, 120° C.) showed that this sample contained 26 methyl-ended branches per 1000 methylenes. Another experiment run under identical conditions afforded 0.17 g of polymer; three other experiments in which 0.12 mmol of 2,6-diisopropylaniline were employed (other conditions the same as above) afforded 0.30 g, 0.20 g, and 0.64 g of polymer.

EXAMPLE 8

Under a nitrogen atmosphere, Ni(COD)$_2$ (0.017 g, 0.06 mmol) and 2,6-diethylaniline (0.018 g, 0.12 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 14 h at 25° C. The final reaction mixture contained polyethylene, which was filtered off, washed with methanol and dried; yield of polymer =0.34 g. $T_m$=122.5° C. (second heat) as determined by DSC.

EXAMPLE 9

Under a nitrogen atmosphere, $Ni(COD)_2$ (0.017 g, 0.06 mmol) and aniline (0.011 g, 0.12 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 14 h at 25° C. The final reaction mixture contained polyethylene, which was filtered off, washed with methanol and dried; yield of polymer =0.049 g. $T_m$=112.0° C. as determined by differential scanning calorimetry.

EXAMPLE 10

Under a nitrogen atmosphere, $Ni(COD)_2$ (0.017 g, 0.06 mmol) and 1,8-diaminonaphthalene (0.010 g, 0.06 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 18 h at 25° C. The final reaction mixture contained polyethylene, which was washed with methanol and dried; yield of polymer =5.38 g. DSC on this sample showed a very broad melting point, $T_m$=37.0° C. (second heat).

EXAMPLE 11

Under a nitrogen atmosphere, $Ni(COD)_2$ (0.017 g, 0.06 mmol) and compound (XII) (0.016 g, 0.12 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 18 h; during this time the temperature inside the reactor varied between 25 and 33° C. The final reaction mixture contained polyethylene, which was filtered off, washed with methanol and dried; yield of polymer =0.13 g. $T_m$=119.3, 129.0° C. as determined by DSC.

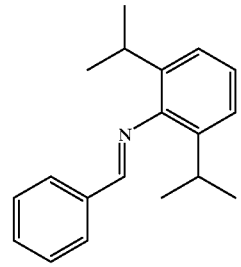

(XII)

EXAMPLE 12

Under a nitrogen atmosphere, $Ni(COD)_2$ (0.017 g, 0.06 mmol) and ortho-phenylenediamine (0.013 g, 0.12 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 18 h at 25° C. The final reaction mixture contained polyethylene, which was filtered off, washed with methanol and dried; yield of polymer =0.052 g. $T_m$=98.0, 119.0° C. as determined by DSC.

EXAMPLE 13

Under a nitrogen atmosphere, $Ni(COD)_2$ (0.017 g, 0.06 mmol) and compound (XIII) (0.013 g, 0.06 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 18 h at 25° C. The final reaction mixture contained polyethylene, which was filtered off, washed with methanol and dried; yield of polymer =0.76 g.

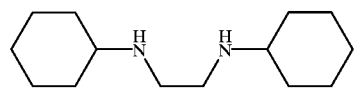

(XIII)

EXAMPLE 14

Under a nitrogen atmosphere, $Ni(COD)_2$ (0.017 g, 0.06 mmol) and compound (XIV) (0.030 g, 0.06 mmol) were dissolved in benzene (5.0 mL). To the resulting solution was added HBAF' $(Et_2O)_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa $C_2H_4$ for 18 h; during this time the temperature inside the reactor varied between 25 and 33° C. The final reaction mixture contained polyethylene, which was filtered off, washed with methanol and dried; yield of polymer =0.039 g. $T_m$=126.2° C. as determined by DSC.

(XIV)

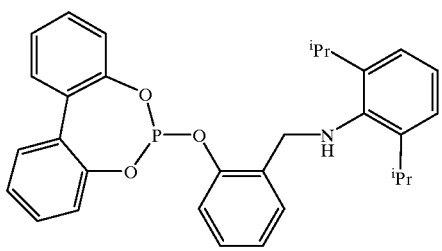

EXAMPLE 15

Under a nitrogen atmosphere, Ni(COD)$_2$ (0.017 g, 0.06 mmol) and anthranilic acid (0.008 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h; during this time the temperature inside the reactor varied between 25 and 39° C. The final reaction mixture contained polyethylene, which was filtered off, washed with methanol and dried; yield of polymer =1.74 g. T$_m$=118.4° C. as determined by DSC.

EXAMPLE 16

Under a nitrogen atmosphere, Ni(COD)$_2$ (0.017 g, 0.06 mmol) and compound (XXXVIII) (0.008 g, 0.06 mmol) were dissolved in benzene (5.0 mL). To the resulting solution was added HBAF' (Et$_2$O)$_2$ (0.060 g, 0.06 mmol). The resulting solution was immediately frozen inside a 40 mL shaker tube glass insert. The glass insert was transferred to a shaker tube, and its contents allowed to thaw under an ethylene atmosphere. The reaction mixture was agitated under 6.9 MPa C$_2$H$_4$ for 18 h; during this time the temperature inside the reactor varied between 25 and 34° C. The final reaction mixture contained polyethylene, which was filtered off, washed with methanol and dried; yield of polymer =1.20 g. T$_m$=120.2, 132.3° C. as determined by DSC.

(XXXVIII)

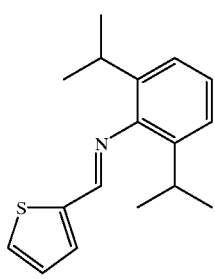

EXAMPLE 17

Synthesis of (VII)

2,6-diisopropylaniline (17.7 g, 100 mmol), 1,2-dibromoethane (9.4 g, 50 mmol), and diisopropylethylamine (20 mL) were heated to reflux for 2 days. Excess diisopropylethylamine was removed from the white crystals in vacuo, and the residue was washed with CH$_2$Cl$_2$. The CH$_2$Cl$_2$ was evaporated to give a red-brown residue. The crude product was recrystallized from methanol to afford white crystals of (VII).

EXAMPLE 18

Synthesis of (IX)

2,6-Diisopropylaniline (0.89 g, 5.0 mmol) and pentafluorobenzaldehyde (0.98 g, 5.0 mmol) were dissolved in CH$_2$Cl$_2$ (20 mL) and the reaction mixture was stirred overnight at room temperature. The solvent was removed in vacuo to afford 1.5 g of (IX) as an off-white solid.

EXAMPLE 19

Synthesis of (X)

1,1'-Biphenyl-2,2'-diylphosphorochloridite (0.251 g, 1.0 mmol) was dissolved in anhydrous diethyl ether (15 mL) under nitrogen. To this stirred solution was slowly added the sodium salt of salicylaldehyde-2,6-diisopropylanilineimine (0.303 g, 1.0 mmol). The solution was stirred for one hour, and then filtered. The filtrate was evaporated to afford a yellow oil. The oil was redissolved in approximately 3–4 mL petroleum ether. Slow evaporation of the solution at room temperature gave yellow crystals of (X). $^1$H NMR (CDCl$_3$) d 8.55 (s, 1H, N=CH), 8.25 (d, 1H, H$_{aryl}$), 7.50–7.05 (mult, 15H, H$_{aryl}$), 2.95 (sept, 2H, CHMe$_2$), 1.15 (d, 12H, CHMe$_2$); $^{31}$P NMR (CDCl$_3$) d 142.44.

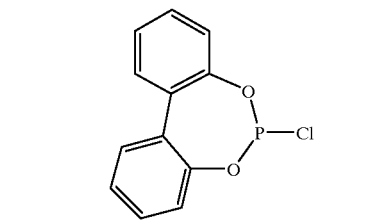

1,1'-biphenyl-2,2'-diylphosphorochloridite

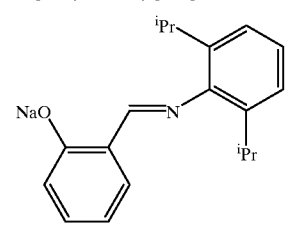

salicylaldehyde-2,6-diisopropylanilineimine sodium salt

The preparation of 1,1'-biphenyl-2,2'-diylphosphorochloridite can be found in the following references: WO 9303839, U.S. Pat. Nos. 4,769,498, and 4,688,651, and Cuny, G. D., et al., J. Am. Chem. Soc. vol. 115, p. 2066 (1993).

Salicylaldehyde-2,6-diisopropylanilineimine was prepared by stirring an equimolar mixture of salicylaldehyde and 2,6-diisopropylaniline in the presence of a catalytic amount of formic acid in methanol for several days at room temperature; the product was from pentane at −78° C. The sodium salt was prepared by reaction with sodium hydride in THF.

EXAMPLE 20

Synthesis of (XI)

Compound (X)I was prepared by the method of Example 19 from 6-chloro-6H-dibenz[c,e][1,2]oxaphosphorin and the sodium salt of salicylaldehyde-2,6-diisopropylanilineimine. $^1$H NMR (CDCl$_3$) d 8.20–7.00 (mult, 16H, N=CH and H$_{aryl}$), 2.80 (sept, 2H, CHMe$_2$), 1.03 (overlapping d's,CHMe$_2$, 12H); $^{31}$P NMR (CDCl$_3$) d 128.8 ppm.

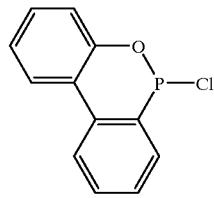

6-Chloro-6H-dibenz [c, e] [1, 2] oxaphosphorin

6-Chloro-6H-dibenz[c,e][1,2]oxaphosphorin was prepared according to a published procedure: Pastor, S. D., et al., *Phosphorus and Sulfur* vol. 31, p. 71 (1987).

EXAMPLE 21

Synthesis of (XIV)

1,1'-biphenyl-2,2'-diylphosphorochloridite (0.125 g, 0.50 mmol) was dissolved in 15 mL 1:1 anhydrous ether/tetrahydrofuran under nitrogen. To this stirred solution was added the sodium salt of N-(ortho-hydroxy)benzyl-2,6-diisopropylaniline (0.153 g, 0.50 mmol). Stirring was continued for another 5.5 hours before the solution was filtered. Evaporation of the filtrate afforded a nearly colorless oil. This material was redissolved in diethyl ether/petroleum ether (~1:2), and the solution cooled to −40° C. A small amount of material precipitated from the solution and was removed. Slow evaporation of the solution afforded white crystals of compound XIV. $^1$H NMR (CDCl$_3$) d 7.60–7.00 (mult, 15H, H$_{aryl}$), 4.05 (s, 2H, CH$_2$), 3.40 ppm (br s, 1H, NH), 3.25 (sept, 2H, CHMe$_2$); 1.10 (d, 12H, CHMe$_2$).

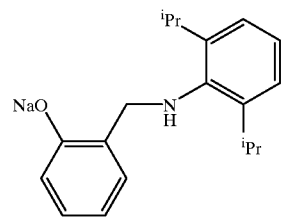

N-(ortho-hydroxy)benzyl-2,6-diisopropylaniline sodium salt

N-(ortho-hydroxy)benzyl-2,6-diisopropylaniline was prepared by NaBH$_4$ reduction of salicylaldehyde-2,6-diisopropylanilineimine in CH$_3$OH/CHCl$_3$ (chloroform was added to help solubilize the aniline starting material). The sodium salt of this compound was prepared by reaction with sodium hydroxide in tetrahydrofuran.

EXAMPLE 22

Synthesis of (VIII)

Compound (VIII) was prepared by reduction of N-(ortho-diisopropylphosphinoxy)benzyl-2,6-diisopropylanilineimine with 2 equivalents of i-Bu$_2$AlH in toluene at 0° C., followed by warming to room temperature and a basic workup.

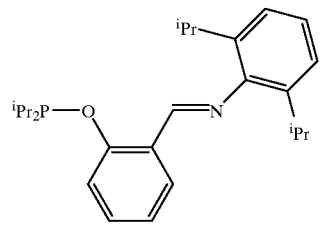

N-(ortho-diisopropylphosphinoxy)benzyl-2,6-diisopropylanilineimine

N-(ortho-diisopropylphosphinoxy )benzyl-2,6-diisopropylanilineimine was prepared by reaction of salicylaldehyde-2,6-diisopropylanilineimine with chlorodiisopropylphosphine and triethylamine in toluene at room temperature.

EXAMPLES 23–66

These Examples were all done by the same general procedure. Under a nitrogen atmosphere, Ni(COD)$_2$ (0.017 g, 0.06 mmol) and the ligand to be tested (0.06 or 0.12 mmol) were dissolved in benzene (5.0 mL). To the resulting solution was added HBAF (Et$_2$O)$_2$ (0.060 g, 0.06 mmol). The resulting solution inside a 40 mL shaker tube glass insert was immediately frozen in a freezer inside the glove box. The glass insert was transferred to a shaker tube, and its contents allowed to thaw under an ethylene atmosphere of 6.9 MPa. The reaction mixture was agitated under 6.9 MPa of ethylene pressure for about 18 h. Any polyethylene in the final reaction mixture was washed with methanol and dried. Melting points of some of the polymers were determined by DSC. These (when determined) along with polymer yields and other data are given in Table 1. The structures of the ligands (except if already shown above) are listed after Table 1.

TABLE 1

| Ex. | Ligan | Ligand/ | g PE | Tm, ° C. |
|---|---|---|---|---|
| 23 | 50 | 1.0 | 24.4 | 123 |
| 24 | 51 | 2.0 | 15.5 | 139 |
| 25 | 52 | 1.0 | 11.0 | — |
| 26 | 53 | 2.0 | 10.2 | 124 |
| 27 | 54 | 1.0 | 5.3 | 124 |
| 28 | 55 | 2.0 | 4.6 | 125 |
| 29 | 56 | 1.0 | 4.3 | — |
| 30 | 57 | 1.0 | 4.0 | 136 |
| 31 | 58 | 1.0 | 3.9 | 118 |
| 32 | 59 | 1.0 | 3.6 | — |
| 33 | 60 | 1.0 | 3.1 | 112 |
| 34 | 61 | 1.0 | 3.0 | 124 |
| 35 | 62 | 1.0 | 3.0 | 123 |
| 36 | 63 | 1.0 | 2.9 | 128 |
| 37 | 64 | 2.0 | 2.6 | — |
| 38 | 65 | 1.0 | 2.1 | — |
| 39 | 66 | 1.0 | 1.8 | 131 |
| 40 | 67 | 1.0 | 1.7 | 118 |
| 41 | 68 | 1.0 | 1.6 | 123 |
| 42 | 69 | 1.0 | 1.5 | — |
| 43 | 70 | 1.0 | 1.5 | — |
| 44 | (XIX) | 1.0 | 1.4 | 121 |
| 45 | 71 | 1.0 | 1.3 | — |
| 46 | (XXV) | 1.0 | 1.3 | 126 |
| 47 | 72 | 1.0 | 1.1 | 131 |
| 48 | 73 | 1.0 | 1.0 | — |
| 49 | 74 | 1.0 | 1.0 | 117 |
| 50 | 74 | 1.0 | .9 | — |
| 51 | 77 | 1.0 | .9 | — |
| 52 | 77 | 1.0 | .9 | 124 |

TABLE 1-continued
| 53 | 78 | 1.0 | .8 | — |
| 54 | 79 | 2.0 | .8 | — |
| 55 | 80 | 2.0 | .7 | — |
| 56 | 81 | 1.0 | .7 | 127 |
| 57 | 82 | 1.0 | .7 | 65 |
| 58 | 83 | 2.0 | .6 | — |
| 59 | (XVII | 1.0 | .6 | — |
| 60 | 84 | 1.0 | .6 | — |
| 61 | 85 | 2.0 | .6 | — |
| 62 | 86 | 2.0 | .5 | — |
| 63 | 87 | 1.0 | .5 | — |
| 64 | 88 | 1.0 | .5 | — |
| 65 | 89 | 2.0 | .5 | — |
| 66 | 90 | 1.0 | .4 | — |
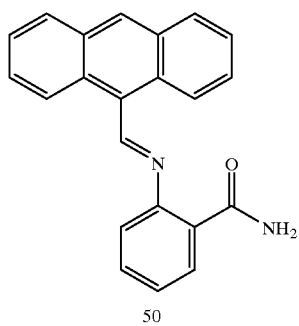
50
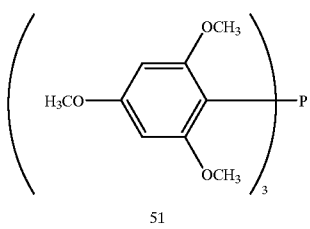
51
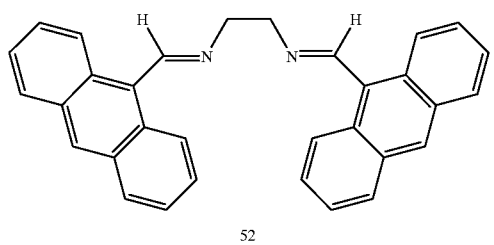
52
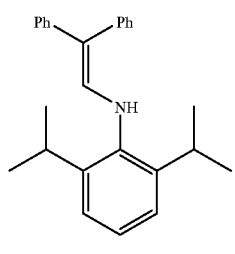
53
TABLE 1-continued
[Structures 54-59 shown]
54
55
56
57
58
59

TABLE 1-continued
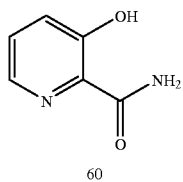
60
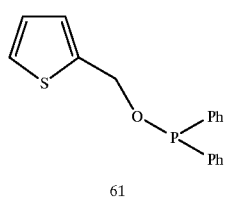
61
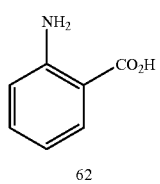
62
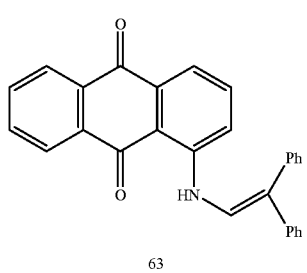
63
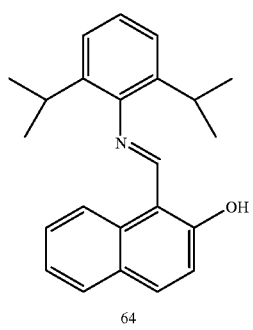
64
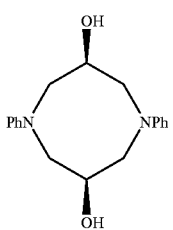
65
TABLE 1-continued
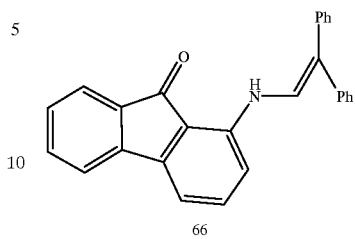
66
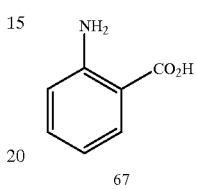
67
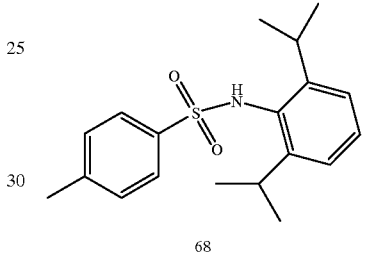
68
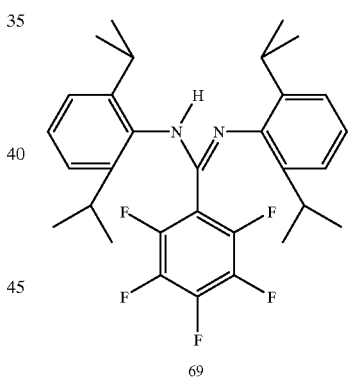
69
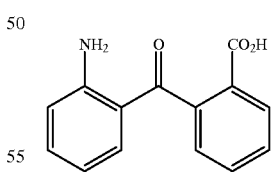
70
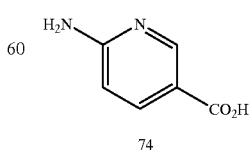
74

TABLE 1-continued
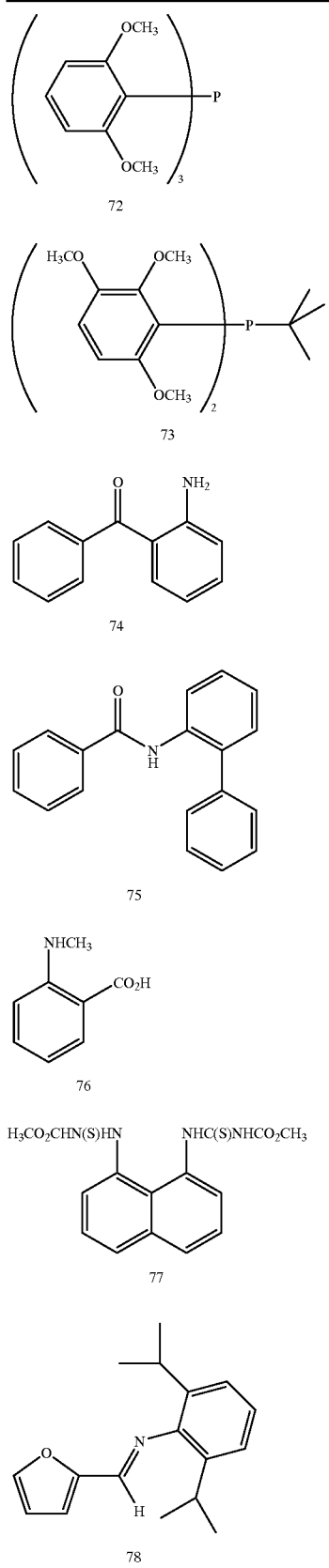
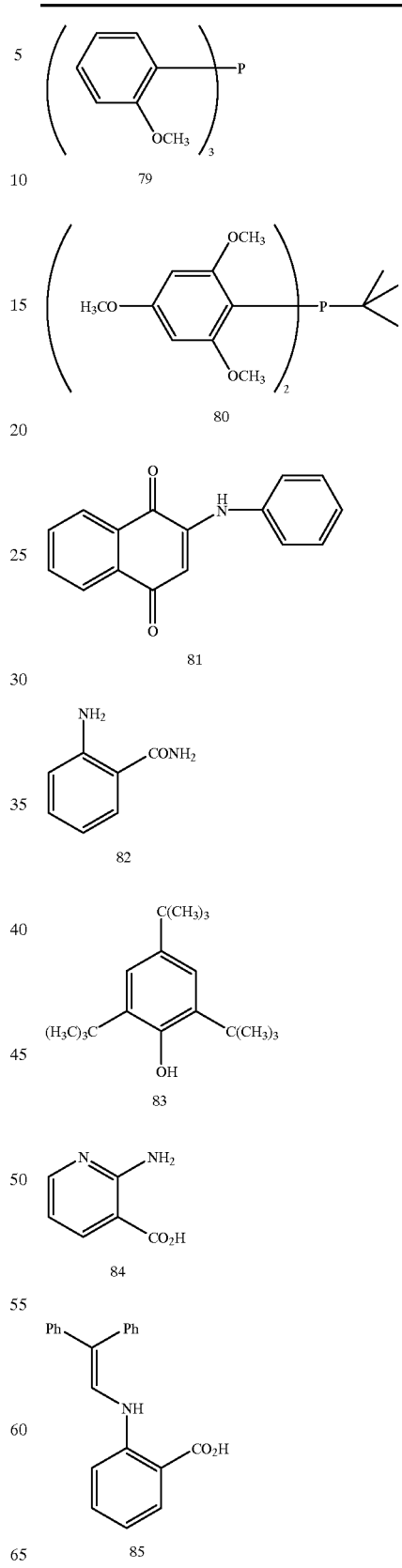

TABLE 1-continued

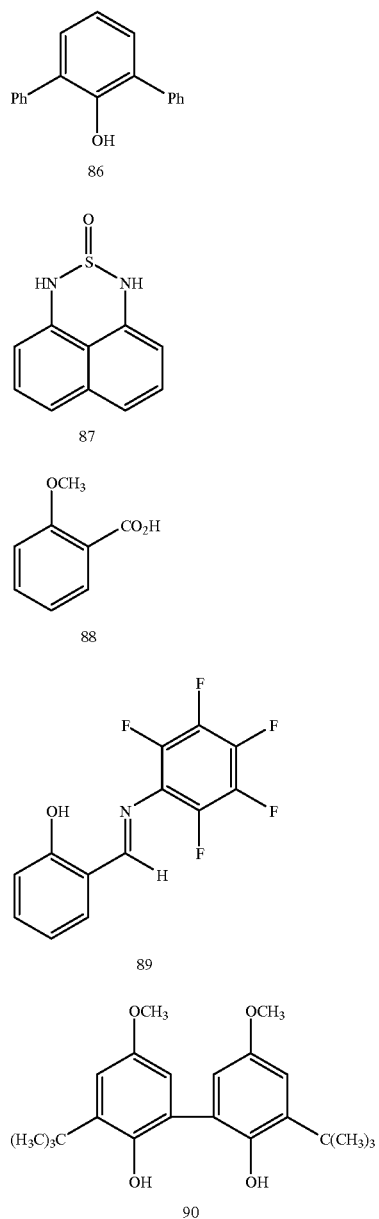

EXAMPLES 67–77

Norbornene Polymerization

General procedure: The reactions were carried out in a dry, deoxygenated atmosphere. The catalyst was weighed into a 20 ml glass scintillation vial and a stir bar was added. A solution of dry dichloromethane/norbornene (3 ml, 43 mass % norbornene) was added and the resulting solutions stirred for 20–90 h. Each product was added to stirring methanol (in air) to precipitate the polymer. The polymer was filtered, washed with methanol/10% HCl solution and methanol and finally dried under vacuum. In each case purity was improved by redissolving the polymer in chloroform and reprecipitating with methanol. $^1$H-NMR (CDCl$_3$) confirmed that the products were addition polymers of norbornene. Details and results of these polymerization are given in Table 2. Structures of the catalysts used are shown after Table 2.

TABLE 2

| Ex. No. | Catalyst | mmol | Time, h | % Yield | Comments |
|---|---|---|---|---|---|
| 67 | 91 | 0.050 | 20 | >95% | Solution was solidified within 5 min. |
| 68 | 92 | 0.041 | 20 | >95% | Solidified over several h |
| 69 | 93[a] | 0.030 | 20 | 93% | Exothermic, boiled solvent |
| 70 | 94 | 0.016 | 44 | 45% | Viscosity increased over several days |
| 71 | 95[a] | 0.036 | 20 | >95% | Exothermic, solidified within 1 min |
| 72 | 96 | 0.010 | 20 | 94% | Solidified over 1 h |
| 73 | 98 | 0.039 | 20 | 85% | No stirring after 20 min (too viscous) |
| 74 | 99 | 0.019 | 20 | 88% | Exothermic, solid within 10 sec |
| 75 | 100 | 0.020 | 20 | 81% | Exothermic, solid within 5 sec |
| 76 | 101 | 0.041 | 20 | >95% | Solidified overnight |
| 77 | 102 | 0.018 | 20 | 87% | Exothermic, solidified rapidly |

[a]End groups visible in $^1$H NMR of polymer indicate lower molecular weight

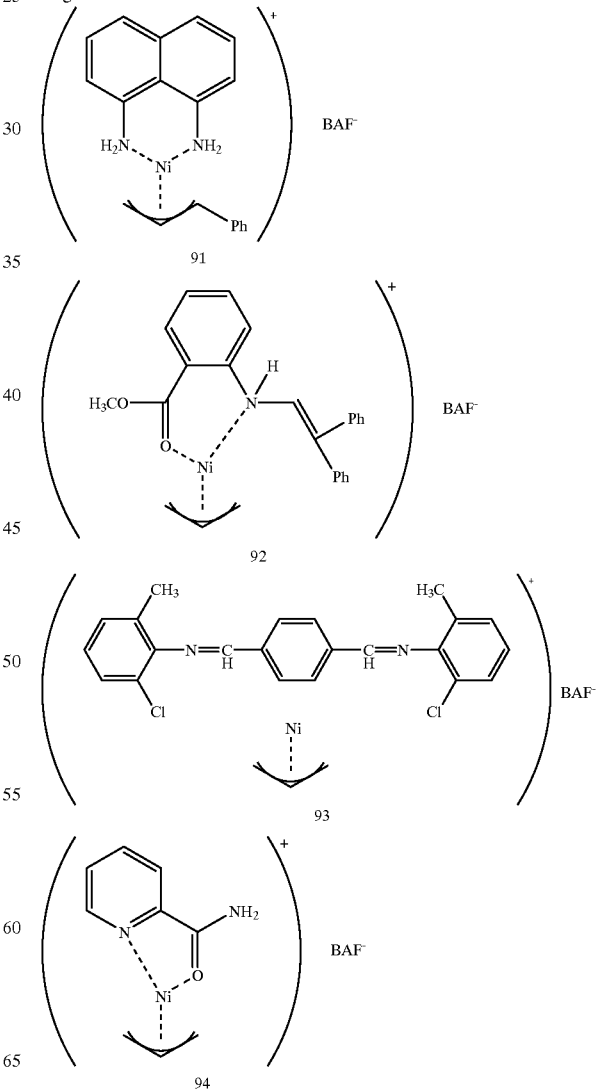

TABLE 2-continued

| Ex. No. | Catalyst | mmol | Time, h | % Yield | Comments |
|---|---|---|---|---|---|

[Structure 95: Ni complex with 2,6-diisopropylaniline ligand, BAF⁻ counterion]

[Structure 96: Ni complex with tris(2,6-dimethoxyphenyl)phosphine ligand, BAF⁻ counterion]

[Structure 96 (variant with CO₂CH₃): Ni complex with tris(2,6-dimethoxyphenyl)phosphine ligand and CO₂CH₃ group, BAF⁻ counterion]

[Structure 98: Ni complex with acenaphthenequinone-derived imine ligand, BAF⁻ counterion]

[Structure 99: Ni complex with 2,6-dimethylaniline imine of pentafluorobenzaldehyde, BAF⁻ counterion]

[Structure 100: Ni complex with diisopropylaniline and 1,1-diphenylethylene-derived ligand, BAF⁻ counterion]

[Structure 101: Ni diimine complex (ethylenediamine bis(2,6-diisopropylaniline)), BAF⁻ counterion]

[Structure 102: Ni complex with 5-methylthiophene-2-carbaldehyde imine of 2,6-diisopropylaniline, BAF⁻ counterion]

EXAMPLES 78–85

Styrene Polymerization

General procedure: The reactions were carried out in a dry, deoxygenated atmosphere. The nickel containing catalyst was weighed into a 20 ml glass scintillation vial and a stir bar added. Dry dichloromethane (2 ml) followed by styrene (2 ml, filtered through alumina, phenothiazine inhibitor) was added and the resulting solutions shaken in the dark for 20 h. The products were added to stirring methanol (in air) to precipitate the polymer. The polymer was filtered, washed with methanol/10% HCl solution and methanol and finally dried under vacuum. Polymers were characterized using $^{13}$C-NMR (CDCl$_3$) which indicated that in each case the product was enriched in racemic diad units relative to atactic polystyrene [for measuring tacticities of polystyrenes see Kawamura, et al., Macromol. Rapid Commun., vol. 15, p. 479–1994)]. Details of each polymerization and results are shown in Table 3. Structures of catalysts are shown after Table 2, above.

TABLE 3

| Ex. No. | Catalyst | mmol | % Yield | Comments |
|---|---|---|---|---|
| 78 | 91 | 0.017 | 37% | Golden solution |
| 79 | 92 | 0.016 | >95% | Brown viscous solution |
| 80 | 93 | 0.015 | 80% | Rapid reaction, viscous brown solution |
| 81 | 95 | 0.017 | 71% | Rapid, orange solution turns brown, viscous |
| 82 | 96 | 0.006 | 6% | Golden solution |
| 83 | 98 | 0.016 | 84% | Boils solvent, dark red viscous solution |
| 84 | 101 | 0.016 | 5% | Yellow solution |
| 85 | 102 | 0.027 | 73% | Yellow solution, rapidly became viscous |

EXAMPLES 86–94

Styrene/Norbornene Copolymerization

General procedure: The reactions were carried out in a dry, deoxygenated atmosphere. The catalyst was weighed into a 20 ml glass scintillation vial and dry dichloromethane (1 ml) and a stir bar added. A solution of dry dichloromethane (2 ml), styrene (2 ml, Aldrich Chemical Co., 99+%, filtered through alumina, phenothiazine inhibitor added) and 1.5 g norbornene (Aldrich Chemical Co., 99%) was added and the resulting solutions shaken in the dark for 20 h. The products were added to stirring methanol (in air) to precipitate the polymer. The polymer was filtered, washed with methanol/10% HCl solution and methanol and finally dried under vacuum.

$^1$H-NMR(CDCl$_3$) indicated that in each case the product contained both styrene and norbornene. The absence of a resonance between 6.2 and 6.7 ppm (assigned to the ortho protons in chains of polystyrene) confirms that the product is a copolymer [see for instance A. Benaboura, et al., C. R. Acad. Sc. Paris, Ser. 2, vol. 301, p. 229 (1985)]. The absence of a polystyrene Tg in the DSC confirmed that the products are copolymers.

Details and results of these polymerization are found in Table 4. Structures of the nickel containing catalysts are shown after Table 2, above.

TABLE 4

| Ex. No. | Catalyst | mmol catalyst | Polymer Yield (g) | Mol % styrene | Comments |
|---|---|---|---|---|---|
| 86 | 91 | 0.019 | 0.72 g | <5% | Golden solution, sticky polymer |
| 87 | 92 | 0.015 | 1.49 g | 11.1% | Brown solution, polymer precipitated |
| 88 | 93 | 0.012 | 2.47 g | 13.7% | Exothermic, precipitated after 5 min |
| 89 | 95 | 0.019 | 2.62 g | 50.8% | Orange solution turned red, precipitated |
| 90 | 97 | 0.013 | 0.28 g | <5% | Brown solution, small amount polymer |
| 91 | 98 | 0.019 | 2.93 g | 41.4% | Red solution, exothermic, precipitated |
| 92 | 99 | 0.009 | 2.64 g | 58.1% | Exothermic, golden solution, precipitated |
| 93 | 100 | 0.015 | 2.15 g | 24.2% | Gold solution, exothermic, precipitated |
| 94 | 101 | 0.023 | 1.54 g | 5.2% | Yellow solution, polymer precipitated |

EXAMPLES 95–107

Following the procedure of Examples 23–66, ethylene was polymerized. The results are reported in Table 5. The structures of the ligands are listed after Table 5.

TABLE 5

| Ex. No. | Ligand | Ligand/Ni | g PE |
|---|---|---|---|
| 95 | 102 | 1.0 | 13.8 |
| 96 | 103 | 1.0 | 11.6 |
| 97 | 104 | 1.0 | 10.8 |
| 98 | 105 | 1.0 | 4.3 |
| 99 | 106 | 1.0 | 1.8 |
| 100 | 107 | 1.0 | 1.5 |
| 101 | 108 | 1.0 | 1.4 |
| 102 | 109 | 1.0 | 1.2 |
| 103 | 110 | 1.0 | 0.9 |
| 104 | 111 | 1.0 | 0.6 |
| 105 | 112 | 1.0 | 0.4 |
| 106 | 113 | 1.0 | 0.4 |
| 107 | 114 | 1.0 | 0.2 |

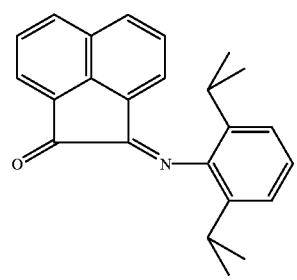

102

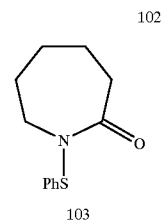

103

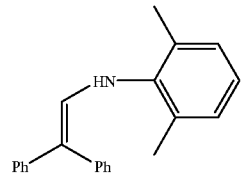

104

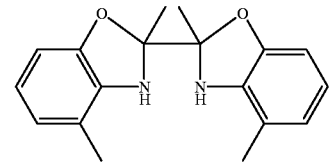

105

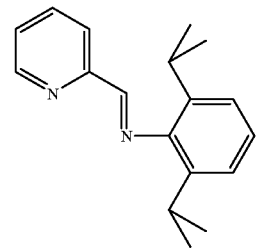

106

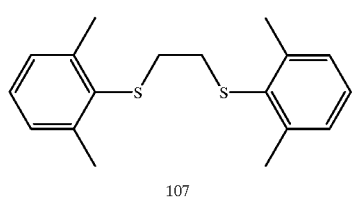

107

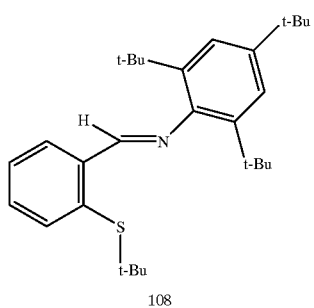

108

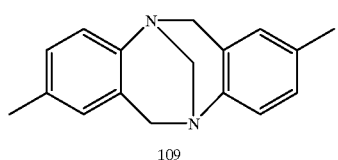

109

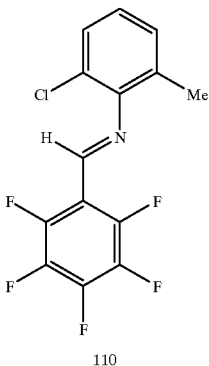

110

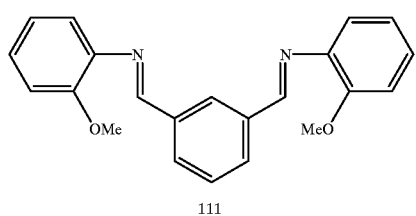

111

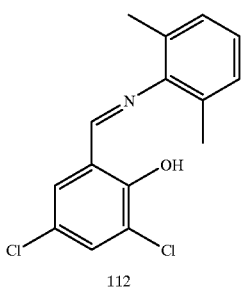

112

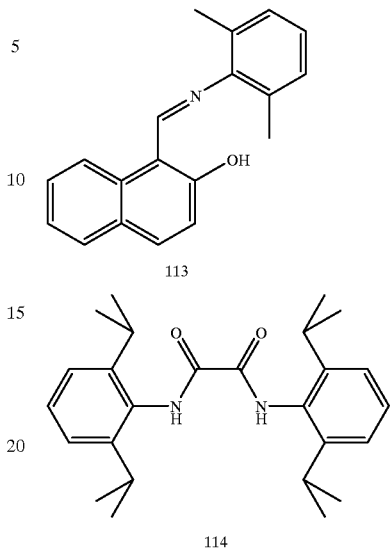

113

114

EXAMPLES 108–183

General Synthesis of Nickel Allyl Initiators. A mixture of one to two equiv. of the appropriate ligand, one equiv of NaBAF, and 0.5 equiv of [(allyl)Ni(m—X)]$_2$ (X=Cl or Br) was dissolved in Et$_2$O. The reaction mixture was stirred for several h before being filtered. The solvent was removed in vacuo to yield the desired product. (The [(allyl)Ni(m—X)]$_2$ precursors were synthesized according to the procedures published in the following reference: Wilke, G., et al., Angew. Chem. Int. Ed. Engl. 1996, 5, 151–164.) The following $^1$H and $^{13}$C spectroscopic assignments of the BAF counterion in CD$_2$Cl$_2$ were invariant for different complexes and temperatures and are not repeated in the spectroscopic data for each of the cationic allyl complexes: [3,5-C$_6$H$_3$-(CF$_3$)$_2$]$_4$$^-$ (BAF). $^1$H NMR (CD$_2$Cl$_2$) d 7.74 (s, 8, H$_o$), 7.57 (s, 4, H$_p$); $^{13}$C NMR (CD$_2$Cl$_2$) d 162.2 (q, J$_{CB}$=37.4, C$_{ipso}$), 135.2 (C$_o$), 129.3 (q, J$_{CF}$=31.3, C$_m$), 125.0 (q, J$_{CF}$=272.5, CF$_3$), 117.9 (C$_p$).

General Procedure for the Screening of Ethylene

Polymerization by Nickel Allyl Initiators. In the drybox, a glass insert was loaded with the isolated allyl initiator synthesized by the above general procedure. The insert was cooled to −35° C. in the drybox freezer, 5 mL of solvent (typically C$_6$D$_6$ or CDCl$_3$) was added to the cold insert, and the insert was then capped and sealed. Outside of the drybox, the cold tube was placed under 6.9 MPa of ethylene and allowed to warm to RT as it was shaken mechanically for approximately 18 h. An aliquot of the solution was used to acquire a $^1$H NMR spectrum. The remaining portion was added to −20 mL of MeOH in order to precipitate the polymer. The polyethylene was isolated and dried under vacuum.

EXAMPLE 108

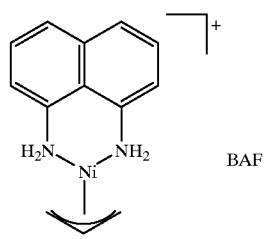

The general synthesis of nickel allyl initiators was followed using 64 mg of ligand, 53 mg of [(C$_3$H$_5$)Ni($\mu$-Cl)]$_2$, and 347 mg of NaBAF. A wheat yellow powder (307 mg) was isolated. $^1$H and $^{13}$C NMR spectra are consistent with the above structure with one equiv of Et$_2$O present. In particular, at −80° C. two sets of amino proton resonances are observed and are coupled to each other. This is consistent with the above structure in which both nitrogen atoms are bound to nickel. At room temperature (20° C.), one broad resonance is observed at 5.64 ppm for all of the amino protons: $^1$H NMR (CD$_2$Cl$_2$, 300 MHz, −80° C.) d 7.81 (d, 2, J=8.09, H$_o$ or H$_p$), 7.41 (t, 2, J=8.1, H$_m$), 7.26 (d, 2, J=6.74, H$_o$ or H$_p$), 5.49 (m, 1, J=6.7, H$_2$CCHCH$_2$), 5.43 (d, 2, J=10.8, NHH'), 5.04 (d, 2, J=12.14, NHH'), 3.38 (br q, 4, J=6.7, O(CH$_2$CH$_3$)$_2$), 3.26 (d, 2, J=6.8 (HH'CCHCHH'), 2.17 (d, 2, J=13.5, HH'CCHCHH'), 0.92 (t, 6, J=6.1, O(CH$_2$CH$_3$)$_2$); $^{13}$C NMR (CD$_2$Cl$_2$, 75 MHz, rt) d 136.1, 130.4, 129.0, 126.7, 123.2 and 121.7 (C$_{aryl}$), 115.4 (H$_2$CCHCH$_2$), 65.9 (H$_2$CCHCH$_2$), 55.7 (O(CH$_2$CH$_3$)$_2$), 14.9 (O(CH$_2$CH$_3$)$_2$).

EXAMPLE 109

The allyl initiator of Example 108 was used to polymerize ethylene in CDCl$_3$ at RT according to the general polymerization procedure using 24 mg of catalyst. Polyethylene was isolated (304 mg).

EXAMPLE 110

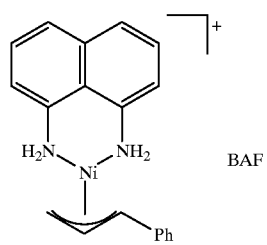

The general synthesis of nickel allyl initiators was followed using 151 mg of ligand, 205 mg of [(H$_2$CCHCHPh)Ni($\mu$-Cl)]$_2$, and 860 mg of NaBAF. A yellow-brown powder (694 mg) was isolated. The $^1$H NMR spectrum indicates that one equiv of Et$_2$O is present. The spectrum, particularly the observation of 4 inequivalent coupled amino protons, is consistent with the above structure in which both nitrogen atoms are bound to nickel. The amino resonances remain inequivalent at least up to 60° C.: $^1$H NMR (CD$_2$Cl$_2$, 300 MHz, −40° C.) d 7.85–7.25 (m, 10, H$_{aryl}$), 6.47 (d, 1, J=6.8, H$_{aryl}$), 6.03 (t of d, 1, J=12.8, 7.2, H$_2$CHCHPh), 5.17 (d, 1, J=10.8, NHH'), 4.89 (d, 1, J=10.8, NHH'), 4.23 (d, 1, J=12.1, N'HH'), 3.73 (d, 1, J=12.1, H$_2$CHCHPh), 3.66 (d, 1, J=10.8, N'HH'), 3.41 (q, 4, J=7.2, O(CH$_2$CH$_3$)$_2$), 3.34 (d, 1, J=6.8, HH'CHCHPh), 2.31 (d, 1, J=12.1, HH'CCHCHPh), 1.05 (t, 6, J=7.4, O(CH$_2$CH$_3$)$_2$).

EXAMPLE 111

The allyl initiator of Example 1110 was used to polymerize ethylene in C$_6$D$_6$ at 80° C. according to the general polymerization procedure using 67 mg of catalyst. No polyethylene was isolated under these conditions. However, the $^1$H NMR spectrum of the reaction mixture indicated that butenes and higher olefins were produced in significant amounts.

EXAMPLE 112

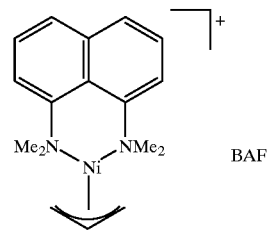

The general synthesis of nickel allyl initiators was followed using 202 mg of ligand, 127 mg of [(C$_3$H$_5$)Ni($\mu$-Cl)]$_2$, and 829 mg of NaBAF. A yellow-orange powder (967 mg) was isolated. The NMR spectra are consistent with the structure shown above, in which both nitrogen atoms coordinate to nickel. $^1$H NMR (CD$_2$Cl$_2$, 300 MHz, rt) d 7.83 (d of d, 2, J=5.9, 3.3, H$_m$), 7.56 (s, 2, H$_o$ or H$_p$), 7.54 (d, 2, J=2.9, H$_o$ or H$_p$), 6.10 (t of t, 1, J=13.4, 7.1, H$_2$CCHCH$_2$), 3.23 (d, 2, J=7.3, HH'CCHCHH'), 3.1 (br, 12, 2×NMe$_2$), 2.58 (d, 2, J=13.2, HH'CCHCHH'); $^{13}$C NMR (CD$_2$Cl$_2$, 75 MHz, rt, nonaromatic carbons only) d 117.6 (H$_2$CCHCH$_2$), 60.2 (H$_2$CCHCH$_2$), 55.1 (br, NMe$_2$).

EXAMPLE 113

The allyl initiator of Example 112 was used to polymerize ethylene in CDCl$_3$ at RT according to the general polymerization procedure (with the exception that 4.1 MPa of ethylene was used) using 40 mg of catalyst. Polyethylene was not isolated. The $^1$H NMR spectrum showed the production of butenes and a small amount of higher olefins.

EXAMPLE 114

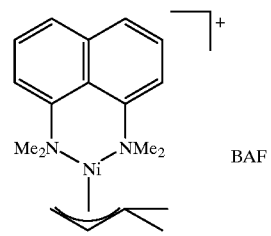

The general synthesis of nickel allyl initiators was followed using 103 mg of ligand, 100 mg of [(H$_2$CCHCMe$_2$)Ni($\mu$-Br)]$_2$, and 427 mg of NaBAF. A pale pink powder (517 mg) was isolated. The NMR spectrum is consistent with the structure shown above, in which both nitrogen atoms coordinate to nickel. $^1$H NMR (CD$_2$Cl$_2$, 300 MHz, rt) d 8.2–7.4 (m, 6, H$_{aryl}$), 5.33 (dd, 1, J=12.8, 7.4, H$_2$CCHCMe$_2$), 3.35–2.80 (br, 12, NMeMe', N'MeMe'), 2.78 (dd, 1, J=8.1, 2.7, HH'CHCMe$_2$), 1.75 (dd, 1, J=13.5, 2.7, HH'CHCMe$_2$), 1.22 and 0.73 (s, 3 each, H$_2$CCHCMeMe').

EXAMPLE 115

The allyl initiator of Example 114 was used to polymerize ethylene in CDCl$_3$ at RT according to the general polymerization procedure using 66 mg of catalyst. Polyethylene was isolated (23 mg).

EXAMPLE 116

The allyl initiator of Example 114 was used to polymerize ethylene in CDCl$_3$ at 80° C. according to the general polymerization procedure using 62 mg of catalyst. No polyethylene was isolated; however, the $^1$H NMR spectrum of the reaction mixture showed the production of butenes, higher olefins, and a broad (CH$_2$)$_n$ peak at 1.25 ppm.

EXAMPLE 117

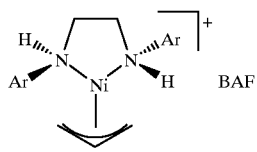

Ar = 2,6-C$_6$H$_3$-i-Pr$_2$

The general synthesis of nickel allyl initiators was followed using 135 mg of ligand, 48 mg of [(C$_3$H$_5$)Ni($\mu$-Cl)]$_2$, and 307 mg of NaBAF. A yellow powder (394 mg) was isolated. The $^1$H and $^{13}$C NMR spectra are consistent with both nitrogen atoms coordinating to nickel, as shown above, with the aryl rings lying trans to each other in the majority of the product. Other isomers may be present in lesser amounts: $^1$H NMR (CD$_2$Cl$_2$, 300 MHz, −40° C.) d 7.4–7.0 (m, 6, H$_{aryl}$), 5.68 (m, 1, H$_2$CCHCH$_2$), 5.53, 5.38, 4.84 and 4.22 (m, 1 each, NCHH'C'HH'N'), 3.4–2.8 (m, 6, NH, N'H, CHMe$_2$, C'HMe$_2$, C''HMe$_2$, C'''HMe$_2$), 2.73 (d, 1, J=6.7, HH'CCHCHH'), 2.62 (d, 1, J=6.8, HH'CCHCHH'), 2.39 (d, 1, J=13.5, HH'CCHCHH'), 1.55 (d, 1, J=13.5, HH'CCHCHH'), 1.8–1.2 (d, 3 each, CHMeMe', C'HMeMe', C''HMeMe', C'''HMeMe'); $^{13}$C NMR (CD$_2$Cl$_2$, 75 MHz, rt) d 140.9, 140.8, 139.9, 139.4, 138.9 and 138.4 (Ar: C$_{ipso}$, C$_o$, C$_o$' and Ar': C$_{ipso}$, C$_o$, C$_o$'), 129.0, 128.8, 127.1, 127.0, 125.4 and 125.1 (Ar: C$_m$, C$_m$', C$_p$ and Ar': C$_m$, C$_m$', C$_p$), 116.1 (H$_2$CCHCH$_2$), 60.7, 55.9, 54.3 and 53.0 (H$_2$CCHCH$_2$, NCH$_2$C'H$_2$N'), 31.7, 30.5, 30.0 and 29.4 (CHMe$_2$, C'HMe$_2$, C''HMe$_2$, C'''HMe$_2$), 26.4, 26.0, 24.4, 24.2, 24.2, 24.2, 24.0 and 22.9 (CHMeMe', C'HMeMe', C''HMeMe', C'''HMeMe').

EXAMPLE 118

The allyl initiator of Example 117 was used to polymerize ethylene in C$_6$D$_6$ at 80° C. according to the general polymerization procedure using 63 mg of catalyst. Polyethylene (3.49 g) was isolated. $^1$H NMR spectrum of the isolated polymer indicates the formation of branched polyethylene with roughly 100 methyl branches per 1000 carbon atoms.

EXAMPLE 119

The allyl initiator of Example 117 was used to polymerize ethylene in CDCl$_3$ at 80° C. according to the general polymerization procedure using 68 mg of catalyst. Polyethylene (1.69 g) was isolated.

EXAMPLE 120

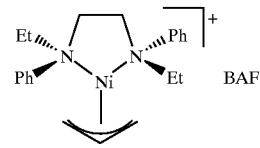

The general synthesis of nickel allyl initiators was followed using 106 mg of ligand, 53 mg of [(C$_3$H$_5$)Ni($\mu$-Cl)]$_2$, and 349 mg of NaBAF. A yellow powder (394 mg) was isolated. The $^1$H and $^{13}$C NMR spectra are consistent with both nitrogen atoms coordinating to nickel, as shown above, with the aryl rings lying trans to each other in the majority of the product. Other isomers may be present in lesser amounts: $^1$H NMR (CD$_2$Cl$_2$, 300 MHz, rt) d 8.3–7.2 (m, 10, H$_{aryl}$), 5.9 (m, 1, H$_2$CCHCH$_2$), 3.9–2.8 (m, 10, HH'CCHCHH', NCH$_2$CH$_2$N', NCH$_2$CH$_3$, N'CH$_2$CH$_3$), 2.49 (d, 1, J=13.6, HH'CCHCHH'), 2.15 (d, 1, J=13.6, HH'CCHCHH'), 1.36 and 1.17 (t, 3 each, J=7.2, NCH$_2$CH$_3$ and N'CH$_2$CH$_3$); $^{13}$C NMR (CD$_2$Cl$_2$, 75 MHz, rt) d 150.1 and 147.5 (Ph: C$_{ipso}$ and Ph': C$_{ipso}$), 130.8, 130.8, 130.8, 130.7, 129.2, 128.9, 128.2, 124.0, 123.9 and 122.6 (Ph: C$_o$, C$_o$', C$_m$, C$_m$' and C$_p$; Ph': C$_o$, C$_o$', C$_m$, C$_m$' and C$_p$), 115.6 (H$_2$CCHCH$_2$), 59.6, 58.7, 58.3, 57.9, 57.3 and 56.4 (H$_2$CCHCH$_2$, NCH$_2$CH$_3$, N'CH$_2$CH$_3$, NCH$_2$CH$_2$N'), 12.6 and 11.8 (NCH$_2$CH$_3$ and N'CH$_2$CH$_3$).

EXAMPLE 121

The allyl initiator of Example 120 was used to polymerize ethylene in CDCl$_3$ at 60° C. according to the general polymerization procedure using 25 mg of catalyst. A few mg's of soft white polyethylene was isolated; the $^1$H NMR spectrum of this product shows branched polyethylene peaks at 1.25 ppm (CH$_2$) and 0.85 ppm (CH$_3$).

EXAMPLE 122

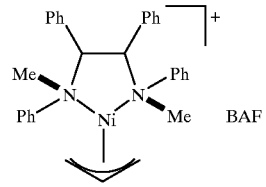

The general synthesis of nickel allyl initiators was followed using 95 mg of ligand, 34 mg of [(C$_3$H$_5$)Ni($\mu$-Cl)]$_2$, and 218 mg of NaBAF. A yellow powder (231 mg) was isolated. The $^1$H NMR spectrum is complex with more than one isomer apparently present.

EXAMPLE 123

The allyl initiator of Example 122 was used to polymerize ethylene in CDCl$_3$ at 60° C. according to the general polymerization procedure using 22 mg of catalyst. A few mgls of polyethylene was isolated; the $^1$H NMR spectrum of this product shows a —(CH$_2$)— peak at 1.2 ppm. The $^1$H NMR spectrum of the reaction mixture shows the production of butenes; branched polyethylene peaks are also observable at 1.25 ppm (CH$_2$) and 0.85 ppm (CH$_3$).

EXAMPLE 124

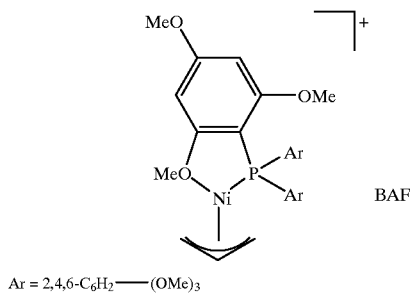

Ar = 2,4,6-C$_6$H$_2$——(OMe)$_3$

The general synthesis of nickel allyl initiators was followed using 213 mg of ligand, 54 mg of [(C$_3$H$_5$)Ni($\mu$-Cl)]$_2$, and 354 mg of NaBAF. An orange powder (391 mg) was isolated. Variable-temperature $^1$H NMR and $^{13}$C NMR spectra are consistent with the above structure in which one methoxy group and the phosphorus atom are coordinated to nickel. $^1$H NMR spectral data are reported at both −100° C. and 20° C. Four resonances for the allyl syn and anti protons are observed at −100° C., while two resonances are observed at RT for these protons. The observation of the four syn and anti protons at −100° C. supports probable coordination of the methoxy group to nickel: $^1$H NMR (CD$_2$Cl$_2$, 300 MHz, −100° C.) d 6.05 (d, 6, J$_{HP}$=4.1, C$_m$), 5.59 (m, 1, H$_2$CCHCH$_2$), 3.89 (d, 1, J=6.75, HH'CHC'HH'), 3.76 (s, p-OMe), 3.67 (s, o-OMe), 3.07 (br s, 1, HH'CHC'HH'), 2.93 (dd, 1, J=13.5, 5.4, HH'CHCHH'), 1.74 (d, 1, J=12.1, HH'CCHCHH'); $^1$H NMR (CD$_2$Cl$_2$, 300 MHz, 20° C.) d 6.13 (d, 6, J$_{HP}$=2.7, C$_m$), 5.62 (m, 1, H$_2$CCHCH$_2$), 3.81 (s, p-OMe), 3.71 (s, o-OMe), 3.49 (d, 2, J=6.8, HH'CHCHH'), 2.42 (d, 2, J=16.2, HH'CHCHH'); $^{13}$C NMR (CD$_2$Cl$_2$, 75 MHz, rt) d 164.0 (C$_p$), 162.4 (d, J$_{CP}$=4.9, C$_o$), 113.7 (H$_2$CCHCH$_2$), 97.8 (d, J$_{CP}$=60.4, C$_{ipso}$ to P), 91.1 (d, J=4.9, C$_m$), 57.8 (H$_2$CCHCH$_2$ and o-OMe, overlapping), 55.4 (p-OMe).

EXAMPLE 125

The allyl initiator of Example 124 was used to polymerize ethylene in CDCl$_3$ at RT according to the general polymerization procedure using 28 mg of catalyst. Butenes were formed according to $^1$H NMR spectroscopy.

EXAMPLE 126

The allyl initiator of Example 124 was used to polymerize ethylene in C$_6$D$_6$ at RT according to the general polymerization procedure using 28 mg of catalyst. Butenes and some higher olefins were formed according to $^1$H NMR spectroscopy.

EXAMPLE 127

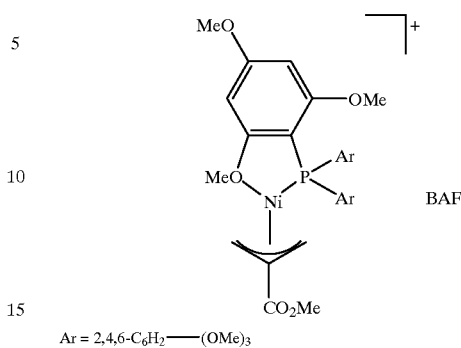

Ar = 2,4,6-C$_6$H$_2$——(OMe)$_3$

The general synthesis of nickel allyl initiators was followed using 501 mg of ligand, 224 mg of [(H$_2$C(CO$_2$Me)CH$_2$)Ni($\mu$-Br)]$_2$, and 834 mg of NaBAF. A yellow-green powder (391 mg) was isolated. $^1$H NMR spectrum of product is complex; the structure shown above is tentatively assigned by analogy to the parent (C$_3$H$_5$) allyl complex.

EXAMPLE 128

The allyl initiator of Example 127 was used to polymerize ethylene in C$_6$D$_6$ at RT according to the general polymerization procedure using 93 mg (0.06 mmol) of catalyst and 2 equiv (29 mg) of BPh$_3$ cocatalyst. Polyethylene (177 mg) was isolated.

EXAMPLE 129

The allyl initiator of Example 127 was used to polymerize ethylene in CDCl$_3$ at RT according to the general polymerization procedure using 93 mg (0.06 mmol) of catalyst and 2 equiv (61 mg) of B(C$_6$F$_5$)$_3$ cocatalyst. Polyethylene (90 mg) was isolated.

EXAMPLE 130

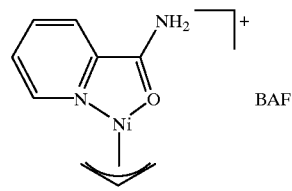

The general synthesis of nickel allyl initiators was followed using 45 mg of ligand, 50 mg of [(C$_3$H$_5$)Ni($\mu$-Cl)]$_2$, and 328 mg of NaBAF. A yellow powder (334 mg) was isolated. The $^1$H NMR spectral data is consistent with the structure shown above: $^1$H NMR (CD$_2$Cl$_2$, 300 MHz, rt) d 8.46 (d, 1, J=5.4, H$_{aryl}$), 8.17 (t, 1, J=8.1, H$_{aryl}$), 7.84 (d, 1, J=8.1, H$_{aryl}$), 7.74 (m, 1, H$_{aryl}$, overlaps with BAF: H$_o$), 7.10 and 6.82 (br s, 1 each NHH'), 5.99 (m, 1, H$_2$CCHCH$_2$), 3.57 (d, 2, J=6.8, HH'CCHCHH'), 2.66 (d, 2, J=13.5, HH'CCHCHH'). $^{13}$C NMR (CD$_2$Cl$_2$, 75 MHz, rt) d 173.5 (C=O), 146.4 (Caryl: C—C(O)NH$_2$), 153.7, 141.4, 131.6 and 123.9 (C$_{aryl}$ attached to hydrogen), 117.2 (H$_2$CCHCH$_2$), (H$_2$CCHCH$_2$ overlaps with CD$_2$Cl$_2$ resonance).

EXAMPLE 131

The allyl initiator of Example 130 was used to polymerize ethylene in CDCl$_3$ at RT according to the general polymerization procedure using 63 mg of catalyst. A few mg's of polyethylene was isolated. According to the $^1$H NMR spectrum of the reaction mixture, significant amounts of butenes and higher olefins were produced. Polyethylene —CH$_2$— resonance is identifiable at 1.25 ppm.

EXAMPLE 132

The allyl initiator of Example 130 was used to polymerize ethylene in C$_6$D$_6$ at 80° C. according to the general polymerization procedure using 64 mg of catalyst. Polyethylene (247 mg) was isolated. According to the $^1$H NMR spectrum of the reaction mixture, the reaction was productive in the formation of butenes and higher olefins.

EXAMPLE 133

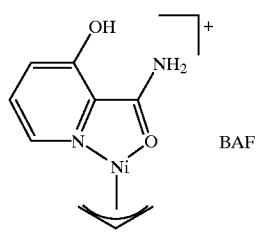

The general synthesis of nickel allyl initiators was followed using 52 mg of ligand, 50 mg of [(C$_3$H$_5$)Ni($\mu$-Cl)]$_2$, and 328 mg of NaBAF. A yellow powder (328 mg) was isolated. The $^1$H NMR spectral data is consistent with the structure shown above: $^1$H NMR (CD$_2$Cl$_2$, 300 MHz, rt) d 11.34 (br s, 1, OH), 8.54 (br s, 1, NHH'), 7.99 (d, 1, J=4.0, H$_{aryl}$), 7.64 (d, 1, J=8.1, H$_{aryl}$) 7.55 (t, 1, J=4.7, H$_{aryl}$), 6.76 (br s, 1, NHH'), 5.95 (m, 1, HH'CCHCHH'), 3.40 (br, HH'CCHCHH', 2.58 (br, HH'CCHCHH'). $^{13}$C NMR (CD$_2$Cl$_2$, 75 MHz, rt, assignments aided by an APT spectrum) δ 173.7 (CO), 155.9 and 133.8 (C$_{aryl}$ not attached to hydrogen), 145.8, 132.3 and 129.3 (C$_{aryl}$ attached to hydrogen), 116.6 (H$_2$CCHCH$_2$), (H$_2$CCHCH$_2$ resonances not observed Neither overlapping with CD$_2$Cl$_2$ resonance or broad and in the baseline).

EXAMPLE 134

The allyl initiator of Example 133 was used to polymerize ethylene in CDCl$_3$ at RT according to the general polymerization procedure using 60 mg of catalyst. Polyethylene (190 mg) was isolated as a white powder.

EXAMPLE 135

The allyl initiator of Example 133 was used to polymerize ethylene in C$_6$D$_6$ at 80° C. according to the general polymerization procedure using 60 mg of catalyst. Polyethylene (783 mg) was isolated. According to the $^1$H NMR spectrum of the reaction mixture, significant amounts of butenes and higher olefins were produced.

EXAMPLE 136

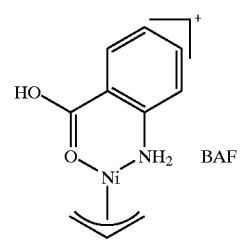

The general synthesis of nickel allyl initiators was followed using 57 mg of ligand, 50 mg of [(C$_3$H$_5$)Ni($\mu$-Cl)]$_2$, and 328 mg of NaBAF. A yellow powder (264 mg) was isolated. The $^1$H, $^{13}$C, and APT NMR spectral data is consistent with the structure shown above: $^1$H NMR (CD$_2$Cl$_2$, 300 MHz, rt) d 14.0 (br s, 1, OH), 8.10 (d, 1, J=8.1, H$_{aryl}$), 7.65 (t, 1, J=8.1, H$_{aryl}$), 7.47 (t, 1, J=8.1, H$_{aryl}$), 7.21 (d, 1, J=8.1, H$_{aryl}$), 5.83 (m, 1, H$_2$CCHCH$_2$), 4.34 (br s, 2, NH$_2$), 3.23 (br d, 2, J=5.4, HH'CCHCHH'), 2.34 (br d, 2, J=13.49, HH'CCHCHH').

EXAMPLE 137

The allyl initiator of Example 136 was used to polymerize ethylene in CDCl$_3$ at RT according to the general polymerization procedure using 63 mg of catalyst. Polyethylene was not isolated. According to the $^1$H NMR spectrum of the reaction mixture, significant amounts of butenes and higher olefins were produced.

EXAMPLE 138

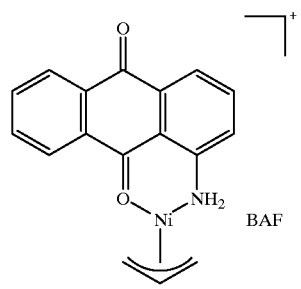

The general synthesis of nickel allyl initiators was followed using 83 mg of ligand, 50 mg of [(C$_3$H$_5$)Ni($\mu$-Cl)]$_2$, and 328 mg of NaBAF. A red powder (381 mg) was isolated. $^1$H NMR (CD$_2$Cl$_2$, 300 MHz, rt): The complex formed a clear red solution in CD$_2$Cl$_2$ with no precipitate present. However, the lock signal and spectrum were both broad, possibly indicating paramagnetism. The above structure is tentatively assigned by analogy to diamagnetic complexes containing ligands with similar donor functionality.

EXAMPLE 139

The allyl initiator of Example 138 was used to polymerize ethylene in CDCl$_3$ at RT according to the general polymerization procedure using 63 mg of catalyst. Polyethylene (88 mg) was isolated.

EXAMPLE 140

The allyl initiator of Example 138 was used to polymerize ethylene in C$_6$D$_6$ at 80° C. according to the general polymerization procedure using 60 mg of catalyst. Polyethylene (64 mg) was isolated. According to the $^1$H NMR spectrum of the reaction mixture, significant amounts of butenes and higher olefins were produced.

EXAMPLE 141

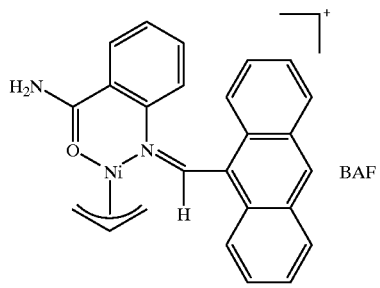

BAF

The general synthesis of nickel allyl initiators was followed using 135 mg of ligand, 50 mg of [(C$_3$H$_5$)Ni($\mu$-Cl)]$_2$, and 328 mg of NaBAF. An orange powder (403 mg) was isolated. The $^1$H, $^{13}$C, and APT NMR spectral data for the major product follows and is consistent with one isomer of the above structure. Other isomers may be present in lesser amounts: $^1$H NMR (CD$_2$Cl$_2$, 300 MHz, rt) d 9.77 and 8.83 (s, 1 each, N=CH and H$_{aryl}$), 9.0–7.5 (m, 8, H$_{aryl}$), 6.91 and 6.63 (br s, 1 each, NHH'), 4.6 (br s, 1, H$_2$CCHCH$_2$), 3.5–2.3 (broad resonances in the baseline, HH'CCHCHH'). $^{13}$C NMR (CD$_2$Cl$_2$, 75 MHz, rt, assignments aided by an APT spectrum) d 173.7 (N=CH), 172.9 (CO), 147.4, 131.6, 131.0, 126.5 and 124.7 (C$_{aryl}$ not attached to hydrogen), 136.8, 133.7, 130.3, 130.2, 129.5, 129.3, 127.0, 123.3 and 122.7 (C$_{aryl}$ attached to hydrogen), 113.8 (H$_2$CCHCH$_2$), (H$_2$CCHCH$_2$ resonances were not observed Neither overlapping with CD$_2$Cl$_2$ resonance or broad and in the baseline).

EXAMPLE 142

The allyl initiator of Example 141 was used to polymerize ethylene in CDCl$_3$ at RT according to the general polymerization procedure using 68 mg of catalyst. Polyethylene (1.60 g) was isolated as a wax.

EXAMPLE 143

The allyl initiator of Example 141 was used to polymerize ethylene in C$_6$D$_6$ at 80° C. according to the general polymerization procedure using 60 mg of catalyst. Polyethylene (5.64 g) was isolated as a wax.

EXAMPLE 144

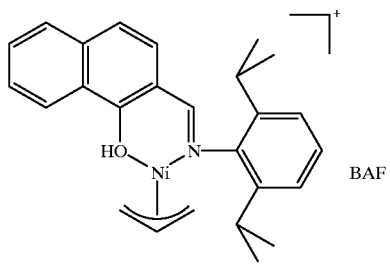

BAF

The general synthesis of nickel allyl initiators was followed using 123 mg of ligand, 50 mg of [(C$_3$H$_5$)Ni($\mu$-Cl)]$_2$, and 328 mg of NaBAF. A yellow powder (383 mg) was isolated. The $^1$H NMR spectrum is consistent with the above structure, although contamination by free ligand is indicated: $^1$H NMR (CD$_2$Cl$_2$, 300 MHz, rt, i-Pr and allyl resonances only) d 5.97 (m, 1, H$_2$CCHCH$_2$), 3.76 (br septet and br d, 1 each, CHMe$_2$ and HH'CHCHH'), 3.53 (br d, 1, J~5.5, HH'CCHCHH'), 3.35 (br septet, 1, C'HMe$_2$), 2.53 (br d, 1, J=13.6, HH'CCHCHH'), 2.20 (br d, 1, J=13.6, HH'CCHCHH'), 1.45, 1.43, 1.29 and 1.15 (d, 3 each, J=6.6–7.7, CHMeMe' and C'HMeMe').

EXAMPLE 145

The allyl initiator of Example was 144 used to polymerize ethylene in CDCl$_3$ at RT according to the general polymerization procedure using 40 mg of catalyst. Polyethylene (30 mg) was isolated as a white powder. According to the $^1$H NMR spectrum of the reaction mixture, significant amounts of butenes and higher olefins were produced. Minor resonances consistent with the formation of branched polyethylene are present.

EXAMPLE 146

The allyl initiator of Example 144 was used to polymerize ethylene in C$_6$D$_6$ at 80° C. according to the general polymerization procedure using 64 mg of catalyst. Polyethylene (96 mg) was isolated as a white powder. The $^1$H NMR spectrum shows the production of butenes and higher olefins. Polyethylene —CH$_2$— resonance is identifiable at 1.25 ppm.

EXAMPLE 147

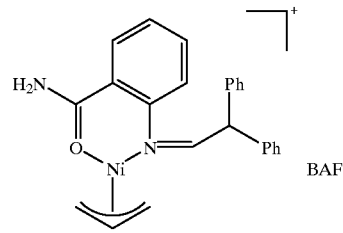

BAF

The general synthesis of nickel allyl initiators was followed using 532 mg of ligand, 229 mg of [(C$_3$H$_5$)Ni($\mu$-Cl)]$_2$, and 1.50 of NaBAF. 1.85 g of a yellow powder was isolated. Although the free ligand exists as the amine, the $^1$H and $^{13}$C NMR spectra are consistent with the ligand binding to the molecule as the imine: $^1$H NMR (THF-d$_8$, 300 MHz, rt) d 8.75 (br s, 2, NH$_2$), 8.55 (d, 1, J=5.4, N=CH), 7.9–7.0 (m, 14, H$_{aryl}$), 5.56 (d, 1, J=5.4, CHPh$_2$), 5.52 (m, 1, H$_2$CCHCH$_2$), 3.01 (d, 2, J=6.7, HH'CCHCHH'), 2.01 (d, 2, J=13.5, HH'CCHCHH'); $^{13}$C NMR (THF-d$_8$, 75 MHz, rt, non-aromatic carbons only, assignments aided by APT spectrum) d 181.7 (N=CH), 172.8 (C=O), 113.8 (H$_2$CCHCH$_2$), 58.7 (CHPh$_2$), 54.5 (H$_2$CCHCH$_2$).

EXAMPLE 148

The allyl initiator of Example 147 was used to polymerize ethylene in CDCl$_3$ at RT according to the general polymerization procedure using 40 mg of catalyst. Polyethylene (25 mg) was isolated as a white powder. According to the $^1$H NMR spectrum of the reaction mixture, butenes were formed along with higher olefins; the major product is consistent with branched polyethylene [1.25 (CH$_2$), 0.85

EXAMPLE 149

The allyl initiator of Example 147 was used to polymerize ethylene in $C_6D_6$ at RT according to the general polymerization procedure using 75 mg of catalyst. Polyethylene (588 mg) was isolated as a white powder.

EXAMPLE 150

The allyl initiator of Example 147 was used to polymerize ethylene in $C_6D_6$ at 80° C. according to the general polymerization procedure using 61 mg of catalyst. Polyethylene (1.39 g) was isolated. According to the $^1$H NMR spectrum of the reaction mixture, significant amounts of butenes and higher olefins were produced. A significant polyethylene —$CH_2$— peak appears at 1.25 ppm.

EXAMPLE 151

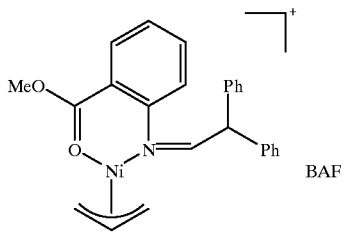

The general synthesis of nickel allyl initiators was followed using 255 mg of ligand, 105 mg of $[(C_3H_5)Ni(\mu\text{-Cl})]_2$, and 685 mg of NaBAF. 772 mg of a pale green powder was isolated.

EXAMPLE 152

The allyl initiator of Example 151 was used to polymerize ethylene in $CDCl_3$ at RT according to the general polymerization procedure using 45 mg of catalyst. Polyethylene (1.61 g) was isolated as a white powder.

EXAMPLE 153

The allyl initiator of Example 151 was used to polymerize ethylene in $C_6D_6$ at RT according to the general polymerization procedure using 62 mg of catalyst. Polyethylene (93 mg) was isolated as a white powder. The $^1$H NMR spectrum shows the production of butenes and higher olefins. Polyethylene —$CH_2$— resonance is identifiable at 1.25 ppm.

EXAMPLE 154

The allyl initiator of Example 151 was used to polymerize ethylene in $C_6D_6$ at 80° C. according to the general polymerization procedure using 67 mg of catalyst. Polyethylene (169 mg) was isolated. According to the $^1$H NMR spectrum of the reaction mixture, the reaction was productive in the formation of butenes and higher olefins. Polyethylene —$CH_2$— resonance is identifiable at 1.25 ppm.

EXAMPLE 155

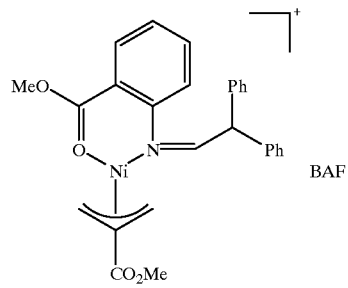

The general synthesis of nickel allyl initiators was followed using 213 mg of ligand, 295 mg of $[(H_2CC(CO_2Me)CH_2)Ni(\mu\text{-Br})]_2$, and 795 mg of NaBAF. A gold powder (0.792 g) was isolated.

EXAMPLE 156

The allyl initiator of Example 155 was used to polymerize ethylene in $C_6D_6$ at RT according to the general polymerization procedure using 61 mg of catalyst. Polyethylene (1.97 g) was isolated as a white powder.

EXAMPLE 157

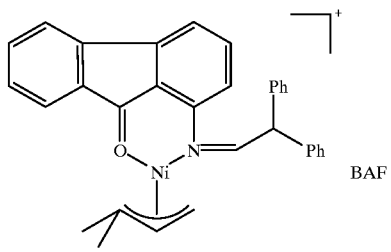

The general synthesis of nickel allyl initiators was followed using 657 mg of ligand, 238 mg of $[(H_2CCHCMe_2)Ni(\mu\text{-Br})]_2$, and 1.56 of NaBAF. A red powder (1.88 g) was isolated. Although the free ligand exists as the amine, the $^1$H and $^{13}$C NMR spectra are consistent with the ligand binding to the molecule as the imine: $^1$H NMR ($CD_2Cl_2$, 300 MHz, rt) d 8.41 (d, 1, J=5.4, N=CH), 7.8–6.8 (m, 17, $H_{aryl}$), 5.42 (d, 1, J=5.4, $CHPh_2$), 4.80 (dd, 1, J=12.8, 6.9, $H_2CCHCMe_2$), 2.95 (d, 1, J=6.7, HH'$CCHCMe_2$), 2.03 (d, 1, J=13.5, HH'$CCHCMe_2$), 0.77 (s, 6, $H_2CCHCMeMe'$); $^{13}$C NMR ($CD_2Cl_2$, 75 MHz, rt, non-aromatic carbons only, assignments aided by APT spectrum) d 202.4 (C=O), 182.6 (N=CH), 109.1 ($H_2CCHCMe_2$), 59.7 ($CHPh_2$), 53.2 ($H_2CCHCMe_2$), 43.1 ($H_2CCHCMe_2$), 26.0 and 20.8 ($H_2CCHCMeMe'$).

EXAMPLE 158

The allyl initiator of Example 157 was used to polymerize ethylene in $C_6D_6$ at RT according to the general polymerization procedure using 61 mg of catalyst. According to the $^1$H NMR spectrum, significant amounts of butenes and higher olefins were produced.

EXAMPLE 159

The allyl initiator of Example 157 was used to polymerize ethylene in $C_6D_6$ at 80° C. according to the general polymerization procedure using 63 mg of catalyst. According to the $^1$H NMR spectrum of the reaction mixture, significant amounts of butenes and higher olefins were produced.

For Examples 160–177 where the ligands are thiophene and furan derivatives, the $^1$H NMR spectra of the products are, in general, complex and include more than one species. The structural assignments of these complexes are therefore tentative.

EXAMPLE 160

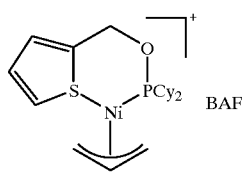

The general synthesis of nickel allyl initiators was followed using 115 mg of ligand, 50 mg of $[(C_3H_5)Ni(\mu\text{-Cl})]_2$, and 328 mg of NaBAF. A sticky dark-red solid (185 mg) was isolated.

EXAMPLE 161

The allyl initiator of Example 160 was used to polymerize ethylene in $CDCl_3$ at RT according to the general polymerization procedure (with the exception that 5.2 MPa of ethylene was used) using 57 mg of catalyst. Polyethylene was not isolated. According to the $^1$H NMR spectrum of the reaction mixture, significant amounts of butenes and higher olefins were produced.

EXAMPLE 162

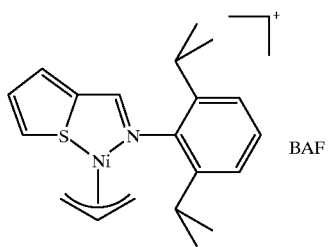

The general synthesis of nickel allyl initiators was followed using 173 mg of ligand, 87 mg of $[(C_3H_5)Ni(\mu\text{-Cl})]_2$, and 570 mg of NaBAF. An orange powder (705 mg) was isolated.

EXAMPLE 163

The allyl initiator of Example 162 was used to polymerize ethylene in $CDCl_3$ at RT according to the general polymerization procedure using 64 mg of catalyst. Polyethylene (72 mg) was isolated. The $^1$H NMR spectrum of the reaction mixture indicates that significant amounts of butenes and higher olefins were produced.

EXAMPLE 164

The allyl initiator of Example 162 was used to polymerize ethylene in $C_6D_6$ at 80° C. according to the general polymerization procedure using 68 mg of catalyst. Polyethylene (77 mg) was isolated. The $^1$H NMR spectrum of the reaction mixture indicates that significant amounts of butenes and higher olefins were produced.

EXAMPLE 165

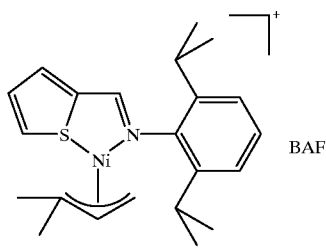

The general synthesis of nickel allyl initiators was followed using 65 mg of ligand, 50 mg of $[(H_2CCHCMe_2)Ni(\mu\text{-Br})]_2$, and 213 mg of NaBAF. An orange powder (163 mg) was isolated.

EXAMPLE 166

The allyl initiator of Example 165 was used to polymerize ethylene in $CDCl_3$ at RT according to the general polymerization procedure using 40 mg of catalyst. Polyethylene (823 mg) was isolated as a white powder.

EXAMPLE 167

The allyl initiator of Example 165 was used to polymerize ethylene in $C_6D_6$ at 80° C. according to the general polymerization procedure using 63 mg of catalyst. Polyethylene was not isolated, however, the $^1$H NMR spectrum of the reaction mixture indicates that significant amounts of butenes and higher olefins were formed.

EXAMPLE 168

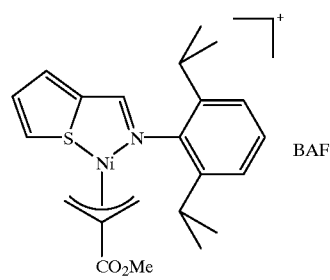

The general synthesis of nickel allyl initiators was followed using 311 mg of ligand, 274 mg of $[(H_2CC(CO_2Me)CH_2)Ni(\mu\text{-Br})]_2$, and 1.02 g of NaBAF. An orange powder (1.30 g) was isolated.

EXAMPLE 169

The allyl initiator of Example 168 was used to polymerize ethylene in $CDCl_3$ at 80° C. according to the general polymerization procedure using 77 mg of catalyst and 1 equiv (31 mg) of $B(C_6F_5)_3$ cocatalyst. Polyethylene (188 mg) was isolated as a waxy solid. The $^1$H NMR spectrum of the reaction mixture indicates that significant amounts of butenes and higher olefins were produced; the polyethylene —$CH_2$— resonance is identifiable at 1.25 ppm.

EXAMPLE 170

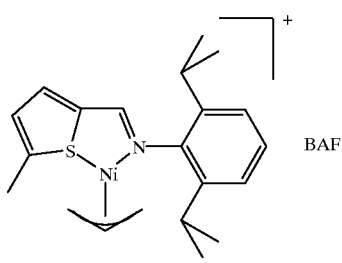

The general synthesis of nickel allyl initiators was followed using 323 mg of ligand, 153 mg of [(C$_3$H$_5$)Ni($\mu$-Cl)]$_2$, and 1.00 g of NaBAF. An orange powder (1.22 g) was isolated.

EXAMPLE 171

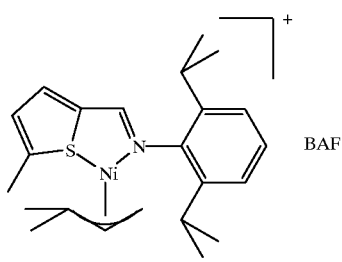

The general synthesis of nickel allyl initiators was followed using 329 mg of ligand, 239 mg of [(H$_2$CCHCMe$_2$)Ni($\mu$-Br)]$_2$, and 1.02 mg of NaBAF. A sticky red solid (742 mg) was isolated.

EXAMPLE 172

The allyl initiator of Example 171 was used to polymerize ethylene in C$_6$D$_6$ at RT according to the general polymerization procedure using 77 mg of catalyst. Polyethylene (100 mg) was isolated. The $^1$H NMR spectrum of the reaction mixture indicates that significant amounts of butenes and higher olefins were produced.

EXAMPLE 173

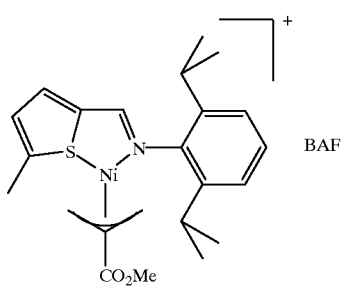

The general synthesis of nickel allyl initiators was followed using 327 mg of ligand, 272 mg of [(C$_3$H$_5$)Ni($\mu$-Cl)]$_2$, and 1.01 g of NaBAF. An orange powder (1.42 g) was isolated.

EXAMPLE 174

The allyl initiator of Example 173 was used to polymerize ethylene in C$_6$D$_6$ at RT according to the general polymerization procedure using 78 mg of catalyst and 2 equiv (29 mg) of BPh$_3$ cocatalyst. Polyethylene was not isolated. The $^1$H NMR spectrum of the reaction mixture indicates that significant amounts of butenes and higher olefins were produced.

EXAMPLE 175

The allyl initiator of Example 173 was used to polymerize ethylene in CDCl$_3$ at 80° C. according to the general polymerization procedure using 78 mg of catalyst and 1 equiv (31 mg) of B(C$_6$F$_5$)$_3$ cocatalyst. Polyethylene (2.39 g) was isolated.

EXAMPLE 176

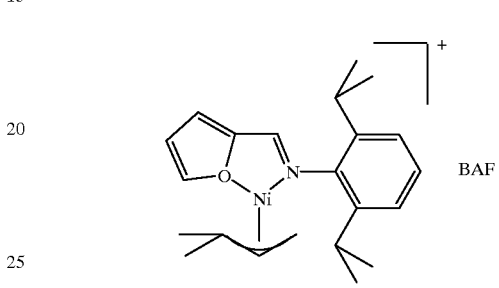

The above general procedure for nickel allyl initiators was followed using 62 mg of ligand, 50 mg of [(H$_2$CCHCMe$_2$)Ni($\mu$-Br)]$_2$, and 213 mg of NaBAF. An orange powder (188 mg) was isolated.

EXAMPLE 177

The allyl initiator of Example 176 was used to polymerize ethylene in CDCl$_3$ at RT according to the general polymerization procedure using 40 mg of catalyst. No polyethylene was isolated.

EXAMPLE 178

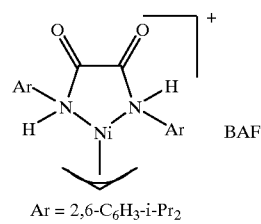

Ar = 2,6-C$_6$H$_3$-i-Pr$_2$

The general synthesis of nickel allyl initiators was followed using 462 mg of ligand, 153 mg of [(C$_3$H$_5$)Ni($\mu$-Cl)]$_2$, and 1.00 g of NaBAF. A beige powder (1.68 g) was isolated. The stability of the complex is poor in CD$_2$Cl$_2$ and THF-d$_8$ at RT. Only broad NMR spectra were obtained. The above structure is therefore tentatively assigned.

EXAMPLE 179

The allyl initiator of Example 178 was used to polymerize ethylene in C$_6$D$_6$ at RT according to the general polymerization procedure using 82 mg of catalyst. Polyethylene was not isolated.

EXAMPLE 180

The allyl initiator of Example 178 was used to polymerize ethylene in CDCl$_3$ at 80° C. according to the general polymerization procedure using 82 mg of catalyst. Polyethylene (2.01 g) was isolated.

EXAMPLE 181

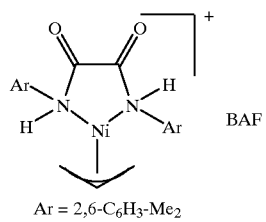

Ar = 2,6-C$_6$H$_3$-Me$_2$

The general synthesis of nickel allyl initiators was followed using 462 mg of ligand, 211 mg of [(C$_3$H$_5$)Ni($\mu$-Cl)]$_2$, and 1.36 mg of NaBAF. A pale orange powder (2.16 g) was isolated. The stability of the complex is poor in CD$_2$Cl$_2$ and THF-d$_8$ at RT. Only broad NMR spectra were obtained. The above structure is therefore tentatively assigned.

EXAMPLE 182

The allyl initiator of Example 181 was used to polymerize ethylene in C$_6$D$_6$ at RT according to the general polymerization procedure using 76 mg of catalyst. Polyethylene (147 mg) was isolated.

EXAMPLE 183

The allyl initiator of Example 181 was used to polymerize ethylene in CDCl$_3$ at 80° C. according to the general polymerization procedure using 76 mg of catalyst. Polyethylene (434 mg) was isolated.

EXAMPLES 184–177

Following the procedure of Examples 23–66, ethylene was polymerized. The results are reported in Table 6. The structures of the ligands are listed after Table 6.

TABLE 6

| Ex. No. | Ligand | Ligand/Ni | g. PE | Tm, ° C. |
|---|---|---|---|---|
| 184 | 115 | 1 | 9.0 | 125 |
| 185 | 116 | 1 | 2.4 | — |
| 186 | 117 | 2 | 2.7 | — |
| 187 | 118 | 1 | 5.0 | — |

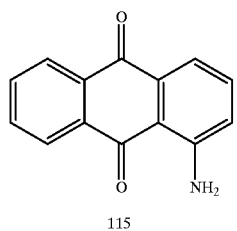

115

TABLE 6-continued

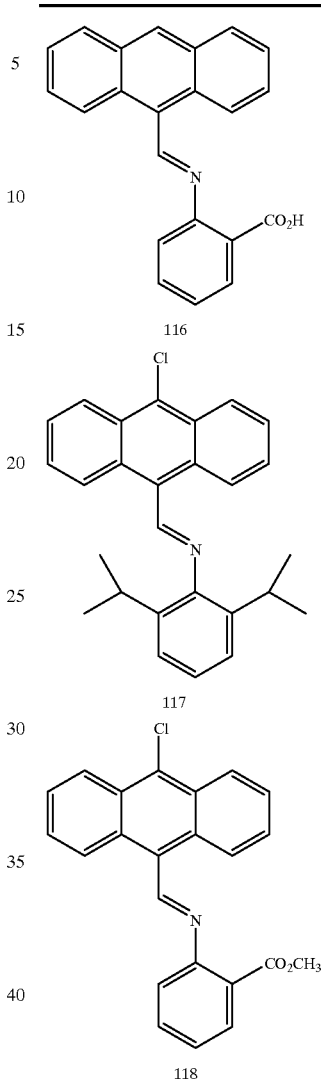

116

117

118

EXAMPLE 188

Synthesis of 50

9-Anthraldehyde (3.70 g) was dissolved in 100 ml THF in a 200 ml round bottom flask. To the hot solution was added dropwise 2.77 g 2-anthranilamide (in 20 ml THF). Then 4 drops of formic acid were added to the mixture. Soon after adding the formic acid, yellow precipitate began to form. Heating and stirring were continued for another 2 h. After cooling, the solid was isolated by filtering, followed by washing with methanol and THF to remove excess 2-anthranilamide. TLC (5:1 hexane:ethyl acetate) showed a single new band. The dried product weighed 3.5 g. $^1$H NMR (DMSO, δ in ppm):9.82(s, 1H);8.90(m, 3H);8.25(m, 3H);7.90(d, 1);7.67.7(m, 7H);7.45(t, 1).

EXAMPLE 189

Synthesis of 66

1,1-Diphenylacetaldehyde (0.4906 g) was dissolved in 30 ml methanol. To this hot solution was added 0.4881 g 1-amino-9-fluorenone (in methanol). Then 6 drops of formic acid was added to catalyze the reaction. Soon after adding the formic acid, the color of the solution changed from yellow to orange red, then to deep red. At this point, TLC (3:1 hexane:ethyl acetate) showed the appearance of new bands. When cooled, a red precipitate formed. The precipitate was isolated by filtering followed by washing with methanol and hexane. The dried product weighed 0.4 g. The $^1$H, $^{13}$C and APT spectra are consistent with the existence of the product as the enamine structure shown above. In addition the structure was confirmed by X-ray crystallography. $^1$H NMR (CD$_2$Cl$_2$, 300 MHz, rt) d 9.25 (d, 1, J=12.1, NH), 7.6–6.85 (m, 18, H$_{aryl}$ and CH=CPh$_2$); $^{13}$C NMR (CD$_2$Cl$_2$, 75 MHz, rt, assignments were aided by an APT spectrum) d 194.0 (C=O), 144.6, 143.1, 142.7, 141.2, 137.7, 134.7 121.3 and 115.15 (C$_{aryl}$ not attached to hydrogen and =CPh$_2$), 136.6, 133.6, 130.1, 129.2, 128.9, 128.3, 127.6, 126.5, 126.1, 123.1, 121.9, 120.4, 112.7 and 110.8 (C$_{aryl}$ attached to hydrogen and =CHNHAr).

EXAMPLE 190

Synthesis of 63

1-Aminoanthraquinone (2.2323 g) was dissolved in a 1:1 mixture of methanol and THF. To the hot solution was added 1.9625 g 1,1-diphenylacetaldehyde. Then 8 drops of formic acid was added as catalyst. After refluxing for 4 h, heating was removed. TLC (5:1 hexane:ethyl acetate) showed the appearance of a new band which was purple. The solvent was removed by rotary evaporator. The solid was resuspended in ether and stirred. Filtered to collect the solid, followed by washing with a large amount of ether until a single band was obtained. Pure product was also obtained by silica gel chromatography to give a purple solid. Yield 1.2 g. $^1$H NMR (CD$_2$Cl$_2$, δ in ppm):11.75(d, 1H) ;8.20(m, 2H);7.25–7.85(m, 16H).

EXAMPLE 191

Synthesis of 54

1,1-Diphenylacetaldehyde (3.9250 g) was dissolved in 30 ml anhydrous methanol. To this refluxing solution was added 2.7230 g 2-anthranilamide (in methanol). Soon a yellow precipitate formed. After all the 2-anthranilamide was added, heating and stirring were continued for another hour. When cooled, the solid was isolated by filtering. The solid was then resuspended in methanol, stirred and then filtered. Yield 5.1 g. The $^1$H, $^{13}$C, and APT spectra are consistent with the existence of the product as the enamine structure shown above: $^1$H NMR (THF-d$_8$, 300 MHz, rt, assignments were aided by an APT spectrum) δ 10.86 (br d, 1, J=12.10, NH—CH=CPh$_2$), 7.60–6.85 (m, 16, H$_{aryl}$, CH=CPh$_2$, C(O)NHH'), 6.60 (br s, 1, C(O)NHH'); $^{13}$C NMR (THF-d$_8$, 75 MHz, rt, assignments were aided by an APT spectrum) δ 171.9 (C=O), 145.9, 143.4, 139.7, 120.0 and 116.6 (C$_{aryl}$ not attached to hydrogen and =CPh$_2$), 113.4, 131.1, 129.4, 128.8, 127.4, 125.9, 124.9, 117.8 and 113.4 (C$_{aryl}$ attached to hydrogen and =CHNAr).

EXAMPLE 192

Synthesis of 56

1,1-Diphenylacetaldehyde (4.0138 g) was dissolved in 20 ml anhydrous methanol. To this hot solution was added 3.0918 g methyl anthranilate (in methanol). The color of the solution changed from colorless to yellow as soon as two components were mixed. After adding all the methyl anthranilate, the heat was turned off. During cooling, a yellow precipitate began to form. The precipitate was collected by filtering followed by washing with methanol. After recrystallization in methanol, 2.6 g product was obtained.

The $^1$H, $^{13}$C, and APT spectra are consistent with the existence of the product as the enamine structure shown above. In addition, this structure was confirmed by X-ray crystallography. $^1$H NMR (CD$_2$Cl$_2$, 300 MHz, rt) δ 9.94 (br d, 1, J=11.73, NH), 8.05–6.75 (m, 15, H$_{aryl}$ and =CHNHAr), 3.78 (s, 3, OMe); $^{13}$C NMR (CD$_2$Cl$_2$, 75 MHz, rt, assignments were aided by an APT spectrum) δ 168.0 (C=O), 145.4, 141.9, 138.4, 120.9 and 112.1 (C$_{aryl}$ not attached to hydrogen and CH=CPh$_2$), 134.6, 132.0, 130.3, 129.0, 128.4, 127.3, 126.7, 125.9, 123.4, 117.7 and 112.4 (C$_{aryl}$ attached to hydrogen and CH=CPh$_2$), 51.8 (OMe).

EXAMPLE 193

Synthesis of 58

9-Anthraldehyde (2.0624 g) was dissolved in 60 ml of a 1:1 mixture of methanol and THF (the 9-anthralaldehyde did not dissolve completely in methanol). To this refluxing solution was added dropwise 1.7729 g 2,6-diisopropylaniline. When the addition was complete, 4 drops of formic acid were added as catalyst. The solution was refluxed for another 2 h before it was cooled. After standing overnight, a yellow solid precipitated. The solid was isolated by filtering followed by washing with methanol. Yield 2.5 g of dried product. $^1$H NMR (CD$_2$Cl$_2$, δ in ppm): 9.51(s, 1H);9.05(d, 2H);9.20(s, 1H);8.20(d, 2H);7.65(m, 4H);7.30 (d, 2H);7.25(t, 1H);3.30(hep, 2H);1.30(d, 12H).

EXAMPLE 194

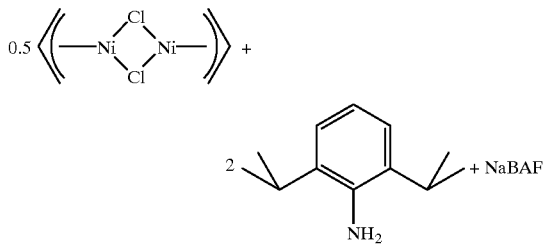

The general synthesis of nickel allyl initiators was followed using 136 mg of ligand, 53 mg of [(C$_3$H$_5$)Ni(μ-Cl)]$_2$, and 342 mg of NaBAF. A yellow powder (430 mg) was isolated.

EXAMPLE 195

The allyl initiator of Example 194 was used to polymerize ethylene in C$_6$D$_6$ at 80° C. according to the general polymerization procedure using 64 mg of catalyst. Polyethylene (104 mg) was isolated. The $^1$H NMR spectrum of the reaction mixture showed that significant amounts of butenes and higher olefins were produced.

EXAMPLE 196

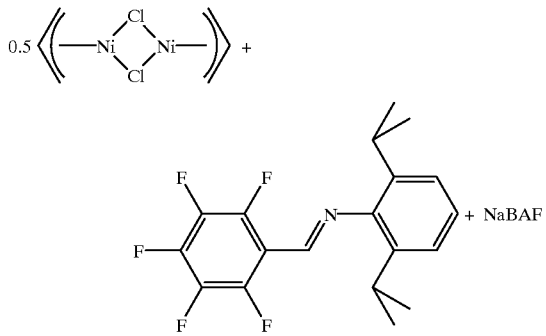

The general synthesis of nickel allyl initiators was followed using 129 mg of ligand, 51 mg of $[(C_3H_5)Ni(\mu\text{-}Cl)]_2$, and 317 mg of NaBAF. A sticky orange solid (217 mg) was isolated.

EXAMPLE 197

The allyl initiator of Example 196 was used to polymerize ethylene in $CDCl_3$ at 60° C. according to the general polymerization procedure using 24 mg of catalyst. The ethylene pressure was initially 1.2 MPa and was increased to 6.9 MPa after 1 h. A few mg's of polyethylene was produced. The $^1H$ NMR spectrum of the reaction mixture showed that significant amounts of butenes and higher olefins were produced.

EXAMPLE 198

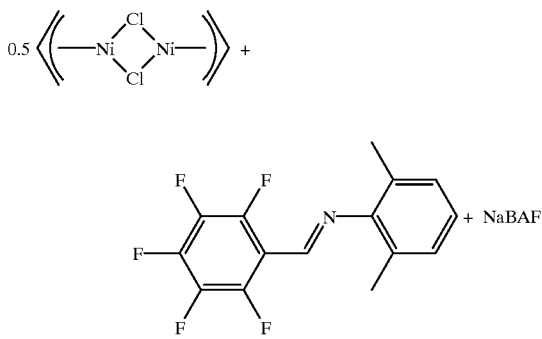

The general synthesis of nickel allyl initiators was followed using 136 mg of ligand, 49 mg of $[(C_3H_5)Ni(\mu\text{-}Cl)]_2$, and 309 mg of NaBAF. An orange powder (380 mg) was isolated.

EXAMPLE 199

The allyl initiator of Example 198 was used to polymerize ethylene in $C_6D_6$ at RT at 5.2 MPa according to the general polymerization procedure using 63 mg of catalyst. Polyethylene (29 mg) was isolated. The $^1H$ NMR spectrum of the reaction mixture showed that significant amounts of butenes and higher olefins were produced.

EXAMPLE 200

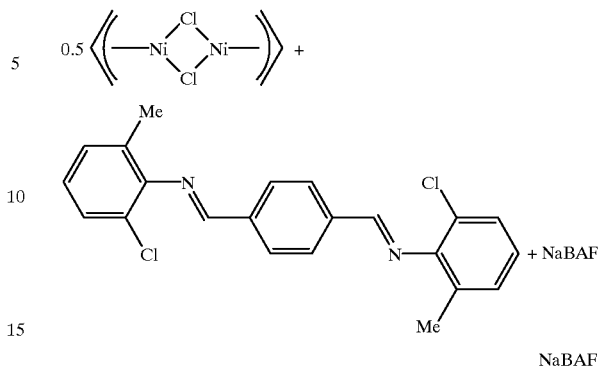

The general synthesis of nickel allyl initiators was followed using 111 mg of ligand, 50 mg of $[(C_3H_5)Ni(\mu\text{-}Cl)]_2$, and 328 mg of NaBAF. An orange powder (347 mg) was isolated.

EXAMPLE 202

The allyl initiator of Example 201 was used to polymerize ethylene in $CDCl_3$ at 60° C. according to the general polymerization procedure using 23 mg of catalyst. The ethylene pressure was initially 1.4 MPa and was increased to 6.9 MPa after 1 h. A few mg's of polyethylene was produced. The $^1H$ NMR spectrum of the reaction mixture showed that significant amounts of butenes and higher olefins were produced.

EXAMPLE 203

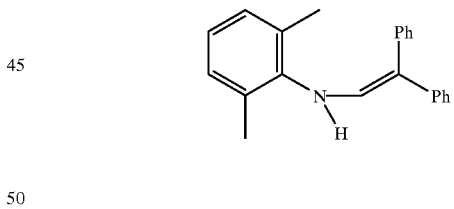

Using 5.47 g of 1,1-diphenylacetaldehyde and 3.60 g of 2,6-dimethylaniline, 5.79 g of an orange powder was obtained following a synthesis analogous to that of the 2,6-diisopropylaniline derivative given above. The $^1H$, $^{13}C$, and APT spectra are consistent with the existence of the product as the enamine structure shown above: $^1H$ NMR ($CDCl_3$, 300 MHz, rt) δ 7.6–7.0 (m, 13, $H_{aryl}$), 6.88 (d, 1, J=12.1, ArNHCH=CPh$_2$), 5.47 (d, 1, J=12.1, ArNHCH=CPh$_2$), 2.37 (s, 6, $C_6H_3$-Me$_2$); $^{13}C$ NMR ($CDCl_3$, 75 MHz, rt, assignments aided by an APT spectrum) δ 142.0, 140.7, 138.9 and 131.1 (Ph: $C_{ipso}$; Ph': $C_{ipso}$; Ar: $C_{ipso}$ and $C_o$), 131.6, 130.6, 129.3, 128.9, 128.3, 126.9, 125.4, 124.8 and 123.8 (Ph: $C_o$, $C_m$, $C_p$; Ph': $C_o$, $C_m$, $C_p$; Ar: $C_m$, $C_p$; CH=CPh$_2$), 114.0 (CH=CPh$_2$), 13.8 ($C_6H_3$-Me$_2$).

EXAMPLE 204

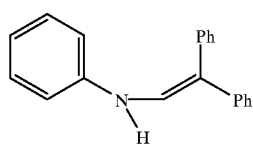

Using 5.43 g of 1,1-diphenylacetaldehyde and 2.71 g of aniline, 5.68 g of yellow powder was obtained following a synthesis analogous to that of the 2,6-diisopropylaniline derivative given above. The $^1$H, $^{13}$C, and APT spectra are consistent with the existence of the product as the enamine structure shown above: $^1$H NMR (CDCl$_3$, 300 MHz, rt) δ 7.6–6.8 (m, 15, H$_{aryl}$), 7.18 (d, 1, J=12.1, PhNHCH=CPh$_2$), 6.12 (d, 1, J=11.8, PhNHCH=CPh$_2$); $^{13}$C NMR (CDCl$_3$, 75 MHz, rt, assignments were aided by an APT spectrum) δ 142.7, 141.8 and 138.5 (Ph: C$_{ipso}$; Ph': C$_{ipso}$; Ph": C$_{ipso}$), 130.5, 129.6, 129.3, 128.4, 127.2, 126.2, 125.5, 124.8, 120.0 and 113.9 (Ph: C$_o$, C$_m$, C$_p$; Ph': C$_o$, C$_m$, C$_p$; Ph": C$_o$, C$_m$, C$_p$; CH=CPh$_2$), 117.7 (CH=CPh$_2$).

EXAMPLE 205

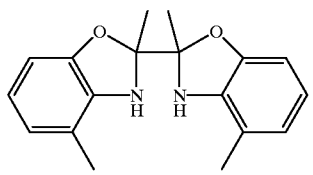

Solution of 1.02 g of 2,3-butanedione in 10 mL of MeOH and 2.92 g of 2-amino-m-cresol were mixed together in a round bottom flask. Formic acid (10 drops) was added via pipette. After ~1.5 h, a precipitate had formed. The solution was stirred overnight and the next day the precipitate was collected on a frit and washed with methanol. The product was then dissolved in Et$_2$O and stirred overnight over Na$_2$SO$_4$. The solution was filtered through a frit with Celite and the solvent was removed in vacuo. A light pink powder was obtained (1.72 g). The $^1$H and $^{13}$C are consistent with the product existing as the cyclized diamine rather than as the diimine. [Note: Literature precedent for this cyclization reaction exists, such as in the reaction of o-aminophenol with glyoxal or the reaction of o-aminobenzoic acid with glyoxal. See: Kliegman, J. M.; Barnes, R. K. *J. Org. Chem.* 1970, 35, 3140–3143.]: $^1$H NMR (CDCl$_3$, 300 MHz, rt) δ 6.9–6.5 (m, 6, H$_{aryl}$) 4.58 (s, 2, NH), 2.20 and 1.62 (s, 6 each, Me, Me'); $^{13}$C NMR (CDCl$_3$, 75 MHz, rt) δ 141.7, 127.1 and 122.3 (Ar: C$_{ipso}$, C$_o$, C$_o$'), 122.6, 119.8, 114.9 (Ar: C$_m$, C$_m$', C$_p$), 82.0 (—OC(Me)NH—), 22.1 and 16.7 (Me, Me').

EXAMPLE 206

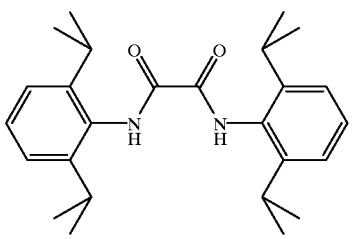

In a nitrogen-filled drybox, 20.01 g of lithium 2,6-diisopropylanilide was placed in a 2-neck round bottom flask and dissolved in 300 mL of Et$_2$O. A 60 mL solution of 6.93 g of oxalyl chloride was placed in an addition funnel. The oxalyl chloride was added to the reaction mixture over a period of several hours and the mixture was then stirred overnight. Some of the product precipitate out of the Et$_2$O solution along with the LiCl. Some of the Et$_2$O was removed in vacuo and enough THF was added to dissolve the product. The solution was filtered through a frit with Celite, the Celite was washed with THF, and the solvent was removed in vacuo. The product was washed with pentane and pumped dry to give 20.72 g of an off-white powder: $^1$H NMR (CDCl$_3$, 300 MHz, rt) δ 9.26 (br s, 2, NH), 7.23–7.04 (m, 6, H$_{aryl}$), 2.94 (septet, 4, CHMe$_2$), 1.09 (d, 24, CHMe$_2$).

EXAMPLE 207

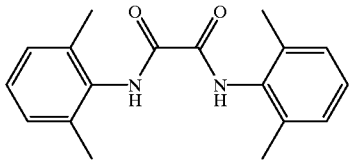

Following the synthetic procedure of the above example, 7.49 g of oxalyl chloride and 15.00 g of lithium 2,6-dimethylanilide was used to synthesize 23.98 g of product, which was isolated as an off-white powder: $^1$H NMR (CDCl$_3$, 300 MHz, rt) δ 9.53 (br 2, 2, NH), 7.00–6.86 (m, 6, H$_{aryl}$), 2.10 (s, 12, Me).

EXAMPLE 208

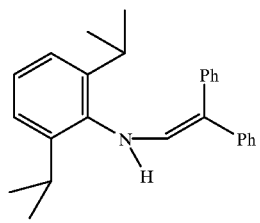

Formic acid catalyst (~1 mL) was added to a methanol solution of diphenylacetaldehyde (4.44 mL) and 2,6-diisopropylaniline (3.18 mL). After ~15 minutes of stirring, a white precipitate formed. The reaction mixture was stirred for several days before the precipitate was collected on a frit and washed with methanol. The product was then dissolved in Et$_2$O and stirred over Na$_2$SO$_4$ overnight. The solution was filtered through a frit with Celite and the solvent was removed in vacuo to yield the product. The $^1$H, $^{13}$C, and APT spectra are consistent with the existence of the product as the enamine structure shown above: $^1$H NMR (CD$_2$Cl$_2$, 300 MHz, rt) δ 7.6–7.0 (m, 13, H$_{aryl}$), 6.71 (d, 1, J=12.1, =CHNHAr), 5.37 (d, 1, J=12.5, NHAr), 3.34 (septet, 2, J=6.9, CHMe$_2$), 1.25 (d, 12, J=7.0, CHMe$_2$); $^{13}$C NMR (CD$_2$Cl$_2$, 300 MHz, rt, assignments were aided by an APT spectrum) δ 144.9 (Ar: C$_o$), 142.5, 139.3 and 138.5 (Ar: C$_{ipso}$, Ph: C$_{ipso}$, Ph': C$_{ipso}$), 133.9, 130.9, 129.7, 128.6, 127.2, 126.2, 125.4, 124.7 and 124.0 (Ph: C$_o$, C$_m$, C$_p$; Ph': C$_o$, C$_m$, C$_p$; Ar: C$_m$, C$_p$, Ph$_2$C=CH), 113.4 (Ph$_2$C=CH), 28.6 (CHMe$_2$), 23.9 (CHMe$_2$).

EXAMPLES 209–217

The imines in the following table were synthesized using Procedures A and B below. Details are shown in the Table.

A. Formic acid catalyst was added to a methanol solution of the aldehyde and the aniline. The reaction mixture was stirred and the resulting precipitate was collected on a frit and washed with methanol. The product was then dissolved in Et$_2$O or CH$_2$Cl$_2$ and stirred over Na$_2$SO$_4$ overnight. The solution was filtered through a frit with Celite and the solvent was removed in vacuo to yield the product.

B. A CH$_2$Cl$_2$ solution of the aldehyde and the aniline was stirred over sodium sulfate. The solution was filtered through a frit with Celite and the solvent was removed in vacuo. If necessary, the product was purified by heating in vacuo to remove excess aniline and/or by recrystallization.

| Example | Ligand | Synthesis and NMR Data |
|---|---|---|
| 209 | | Procedure A, $^1$H NMR (CDCl$_3$, 300 MHz, rt) δ 8.97 (s, 1, CH=N), 8.43 (dd, 1, J = 7.8, 1.6, H$_{aryl}$), 7.64 (dd, 1, J = 7.6, 1.3, H$_{aryl}$), 7.55 (t, 1, J = 7.2, H$_{aryl}$), 7.46 (td, 1, J = 74, 1.7, H$_{aryl}$), 7.37 (s, 2, H$_{aryl}$), 1.37 (s, 9, CMe$_3$), 1.28 (s, 18, CMe$_3$), 1.21 (s, 9, CMe$_3$). |
| 210 | | Procedure A, $^1$H NMR (CDCl$_3$, 300 MHz, rt) δ 15.30 (s, 1, OH), 9.09 (s, 1, N=CH), 8.1–7.2 (m, 9, H$_{aryl}$), 3.12 (septet, 2, CHMe$_2$), 1.25 (d, 12, CHMe$_2$); $^{13}$C NMR (CDCl$_3$, 75 MHz, rt) δ 161.7 (C'N). |
| 211 | | Procedure A. $^1$H NMR (CDCl$_3$, 300 MHz, rt) δ 15.3 (s, 1, OH), 9.23 (s, 1, N=CH), 8.4–7.1 (m, 9, H$_{aryl}$), 2.41 (s, 6, Me). |
| 212 | | Procedure A. $^1$H NMR (CDCl$_3$, 300 MHz, rt) δ 14.15 (s, 1, OH), 8.43 (s, 1, N=CH), 7.7–71 (m, 5, H$_{aryl}$), 2.35 (s, 6, Me). |

-continued

| Example | Ligand | Synthesis and NMR Data |
|---|---|---|
| 213 | (pentafluorophenyl)N=CH-(2-hydroxyphenyl) | Procedure A. $^1$H NMR (CDCl$_3$, 300 MHz, rt) δ 12.27 (s, 1, OH), 8.85 (N=CH), 7.6–6.9 (m, 4, H$_{aryl}$); $^{13}$C NMR (CDCl$_3$, 75 MHz, rt) δ 170.6, 161.5, 134.9, 133.3, 119.5, 118.7 and 117.8 (N=CH, C$_{aryl}$ excluding C$_6$F$_5$ resonances). |
| 214 | (2,6-diisopropylphenyl)N=CH-phenyl | Procedure A. $^1$H NMR (CDCl$_3$, 300 MHz, rt) δ 8.20 (s, 1, N=CH), 8.0–7.0 (m, 8, H$_{aryl}$), 3.00 (septet, 2, CHMe$_2$), 1.21 (d, 12, CHMe$_2$); $^{13}$C NMR (CDCl$_3$, 75 MHz, rt) δ 161.9 (N=CH), 149.3, 137.6, 136.1, 131.3, 128.8, 128.5, 124.1 and 123.0 (C$_{aryl}$), 28.0 (CHMe$_2$), 23.5 (CHMe$_2$). |
| 215 | (2-chloro-6-methylphenyl)N=CH-(pentafluorophenyl) | Procedure A. $^1$H NMR (CDCl$_3$, 300 MHz, rt) δ 8.48 (s, 1, N=CH), 7.35–6.95 (m, 3, H$_{aryl}$), 2.22 (s, 3, Me); $^{13}$C NMR (CDCl$_3$, 300 MHz, rt) δ 153.9 (N=CH), 148.2, 130.4, 128.8, 127.6, 125.5 and 122.6 (C$_{aryl}$ excluding C$_6$F$_5$ resonances), 18.4 (Me). |
| 216 | (2,6-diisopropylphenyl)N=CH-(2-furyl) | Procedure B. $^1$H NMR (CDCl$_3$, 300 MHz, rt) δ 7.99 (s, 1, CH=N), 7.7–6.5 (m, 6, H$_{aryl}$), 3.00 (septet, 2, CHMe$_2$), 1.19 (d, 12, CHMe$_2$); $^{13}$C NMR (CDCl$_3$, 75 MHz, rt) δ 152, 150.4, 149, 145.5, 137.8, 124.3, 123.0, 115.0 and 112.0 (N=CH and C$_{aryl}$), 27.9 (CHMe$_2$), 23.6 (CHMe$_2$). |

-continued

| Example | Ligand | Synthesis and NMR Data |
|---|---|---|
| 217 | 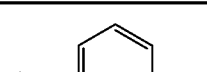 | Procedure B. $^1$H NMR (CDCl$_3$, 300 MHz, rt) δ 8.35 (s, 1, CH=N), 76–7.1 (m, 6, H$_{aryl}$), 3.08 (septet, 2, CHMe$_2$), 1.25 (d, 12, CHMe$_2$); $^{13}$C NMR (CDCl$_3$, 75 MHz, rt) δ 154.9, 148.5, 142.5, 137.8, 131.6, 130.1, 127.6; 124.2 and 122.9 (N=CH and C$_{aryl}$), 27.9 (CHMe$_2$), 23.4 (CHMe$_2$). |

EXAMPLE 218

In a dry and oxygen free atmosphere, the allyl initiator of Example 168 (16 mg) was dissolved in dry CH$_2$Cl$_2$ (2 ml). 5-Ethylidene-2-norbornene (1.8 g) was added. The orange solution warmed and darkened. After stirring for 17 hours the reaction was quenched by addition of methanol and the solid polymer filtered, washed well with methanol and dried. Yield=1.6 g (89%). $^1$H-NMR data confirmed that this was an addition polymer.

EXAMPLE 219

Synthesis of 107

2,6-Dimethylthiophenol (3.0 g) was mixed with 30 ml THF. Then 0.87 g NaOH was added. The mixture was stirred until all the NaOH has dissolved. THF was removed under vacuum. To the solid was added 40 ml DMF and 4.02 g of the bis toluenesulfonate ester of ethylene glycol. The mixture was refluxed for 5–6 h. DMF was removed by rotary evaporator to give a white residue. Water was added to the residue and the mixture extracted with CH$_2$Cl$_2$. After removing CH$_2$Cl$_2$, a white solid remained. TLC (hexane) showed two bands. The second band from a silica-gel column was the desired product.

$^1$H NMR (CDCl$_3$, δ in ppm): 2.43 (s, 12H); 2.72(s, 4H); 7.10(m, 6H).

EXAMPLE 220

Synthesis of 116

9-Anthraldehyde (2.06 g) was dissolved in a minimum amount of THF, then 1.37 g anthranilic acid was added. Four drops of formic acid were added as catalyst. The mixture was refluxed for 7 h. TLC (5:1 hexane:ethyl acetate) gave 3 bands. The second band is the desired product as determined by $^1$H NMR.

EXAMPLE 221

Synthesis of 117

10-chloro-9-anthraldehyde (2.41 g) was dissolved in a mixture of 30 ml THF/20 ml CDCl$_3$/50 ml toluene. To this boiling solution was added dropwise 3.5 g 2,6-diisopropylaniline 3–4 drops of formic acid as a catalyst. The solution was refluxed for 13 h. After removing all the solvent, a dark brown thick oil was left. On standing, the oil crystallized. The crystals were washed with methanol.

$^1$H NMR (CDCl$_3$, δ in ppm): 1.40 (d, 12H); 3.35 (p, 2H); 7.40(m, 3H); 7.75(m, 4H); 8.75(d, 2H); 9.05(d, 2H); 9.55(s, 1H).

EXAMPLE 222

Synthesis of 118

10-Chloro-9-anthraldehyde was (2.41 g) was dissolved in 50 ml toluene, and to the hot solution was added 2.0 g of methyl anthranilate (in THF) dropwise. After refluxing for 6 h, a yellow solid precipitated. The solid was isolated by filtration, followed by washing with methanol. The solid was dissolved in 2–3 ml CDCl$_3$ and after column separation, golden yellow crystals were obtained. $^1$H NMR showed it is a pure product.

$^1$H NMR (DMF-d7, δ in ppm): 4.20(s, 3H); 6.50(d, 1H); 6.82(t, 1H); 7.20(t, 1H); 7.63(t, 2H); 7.80(t, 2H); 8.10(s, 1H); 8.30(d, 1H); 8.30(d, 2H); 9.20(d, 2H).

EXAMPLE 223

In a dry and oxygen free atmosphere, the allyl initiator of Example 168 (16 mg) was dissolved in dry CH$_2$Cl$_2$ (2 ml). Dicyclopentadiene (2 ml) was added. The orange solution darkened. After stirring for 72 h the volatiles were removed from the reaction under vacuum. After addition of methanol the solid polymer precipitated and was filtered, washed well with methanol and dried. Yield=0.29 g (15%). The product was insoluble at room temperature in common organic solvents.

What is claimed is:

1. A compound of the formula $[L^1_q L^2_r L^3_s L^4_t Ni]^+ X^-$ (XXXIII), wherein:

$L^1$ is a first monodentate neutral ligand coordinated to said nickel, $L^2$ is a second monodentate neutral ligand coordinated to said nickel which may be said first monodentate neutral ligand and r is 0 or 1, or $L^1$ and $L^2$ taken together are a first bidentate neutral ligand coordinated to said nickel and r is 1;

$L^3$ and $L^4$ taken together are a π-allyl ligand coordinated to said nickel, $L^3$ and $L^4$ taken together are

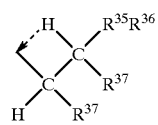

(XXXII)

coordinated to said nickel, or $L^3$ is a third neutral monodentate ligand selected from the group consisting of ethylene, a norbornene and a styrene or a neutral monodentate ligand which can be displaced by an olefin, and $L^4$ is $R^{38}$;

X is a relatively non-coordinating anion;
q, s and t are each 1;
said first monodentate neutral ligand and said first bidentate neutral ligand are selected from the group consisting of

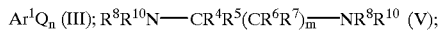
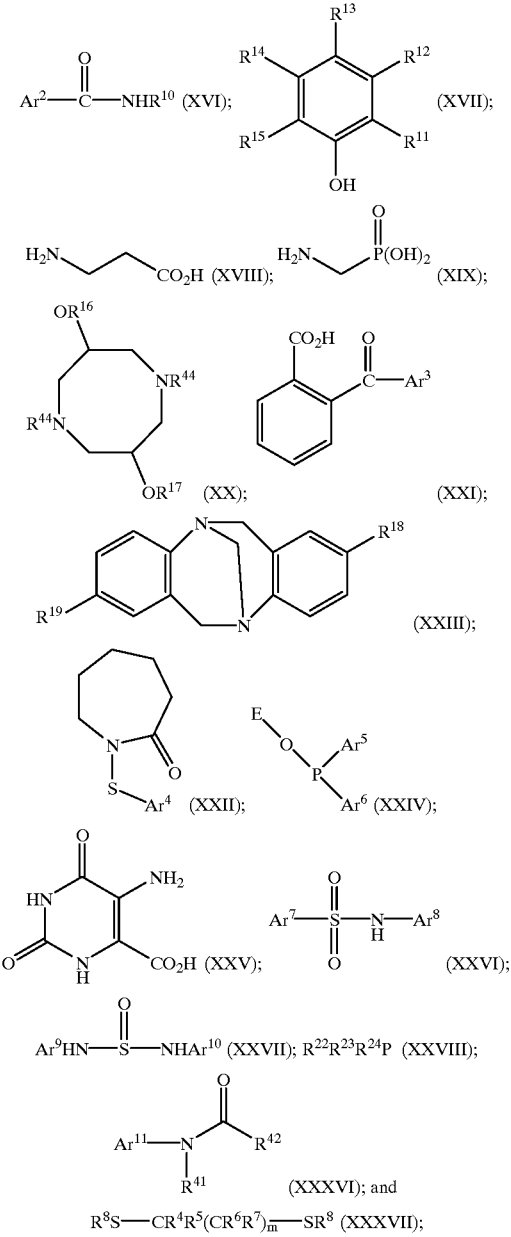

$Ar^1$ is an aromatic moiety with n free valencies, or diphenylmethyl;
each Q is —$NR^2R^{43}$ or —$CR^9$=$NR^3$;
$R^{43}$ is hydrogen or alkyl
n is 1 or 2;
E is 2-thienyl or 2-furyl;
each $R^2$ is independently hydrogen, benzyl, substituted benzyl, phenyl or substituted phenyl;
each $R^9$ is independently hydrogen or hydrocarbyl; and
each $R^3$ is independently a monovalent aromatic moiety;

m is 1, 2 or 3;
each $R^4$, $R^5$, $R^6$, and $R^7$ is independently hydrogen, hydrocarbyl or substituted hydrocarbyl;
each $R^8$ is independently hydrocarbyl or substituted hydrocarbyl containing 2 or more carbon atoms;
each $R^{10}$ is independently hydrogen, hydrocarbyl or substituted hydrocarbyl;
$Ar^2$ is an aryl moiety;
$R^{12}$, $R^{13}$, and $R^{14}$ are each independently hydrogen, hydrocarbyl, substituted hydrocarbyl or an inert functional group;
$R^{11}$ and $R^{15}$ are each independently hydrocarbyl, substituted hydrocarbyl or an inert functional group whose $E_s$ is about −0.4 or less;
each $R^{16}$ and $R^{17}$ is independently hydrogen or acyl containing 1 to 20 carbon atoms;
$Ar^3$ is an aryl moiety;
$R^{18}$ and $R^{19}$ are each independently hydrogen or hydrocarbyl;
$Ar^4$ is an aryl moiety;
$Ar^5$ and $Ar^6$ are each independently hydrocarby;
$Ar^7$ and $Ar^8$ are each independently an aryl moiety;
$Ar^9$ and $Ar^{10}$ are each independently an aryl moiety or —$CO_2R^{25}$, wherein $R^{25}$ is alkyl containing 1 to 20 carbon atoms;
$Ar^{11}$ is an aryl moiety;
$R^{41}$ is hydrogen or hydrocarbyl;
$R^{42}$ is hydrocarbyl or —C(O)—$NR^{41}$—$Ar^{11}$;
$R^{44}$ is aryl;
$R^{22}$ and $R^{23}$ are each independently phenyl groups substituted by one or more alkoxy groups, each alkoxy group containing 1 to 20 carbon atoms; and
$R^{24}$ is alkyl containing 1 to 20 carbon atoms, or an aryl moiety;
$R^{35}$ is hydrocarbylene;
$R^{36}$ is hydrogen, alkyl, or —C(O)$R^{39}$;
each $R^{37}$ is hydrocarbyl or both of $R^{37}$ taken together are hydrocarbylene to form a carbocyclic ring;
$R^{38}$ is hydride, alkyl or —C(O)$R^{39}$; and
$R^{39}$ is hydrocarbyl.

2. The compound as recited in claim 1 wherein X is $BF_4^-$, $PF_6^-$, BAF$^-$, or $SbF_6^-$.

3. The compound as recited in claim 1 wherein said first compound or said first monodentate neutral ligand is (III).

4. The compound as recited in claim 3 wherein:
n is 1, Q is —$CR^9$=$NR^3$, $R^9$ is hydrogen, $Ar^1$ is 9-anthracenyl, and $R^3$ is 2-carbamoylphenyl or 2,6-diisopropylphenyl;
n is 2 and Q is —$CR^9$=$NR^3$, $R^3$ is 2,6-disubstituted phenyl in which substitutents are halo, alkyl, or halo and alkyl, $Ar^1$ is p-phenylene, and $R^9$ is hydrogen;
n is 1, Q is —$CR^9$=$NR^3$, $R^9$ is hydrogen, $R^3$ is 2,6-dimethylphenyl, and $Ar^1$ is pentafluorophenyl; or
n is 1, Q is —$CR^9$=$NR^3$, $R^9$ is hydrogen, $R^3$ is 2,6-diisopropylphenyl, and $Ar^1$ is 2-hydroxy-1-naphthyl.

5. The compound as recited in claim 3 wherein:
n is 1, Q is —$NR^2R^{43}$, $R^2$ is —CH=$CPh_2$, $R^{43}$ is hydrogen, and $Ar^1$ is 2,6-diisopropylphenyl;
n is 1, Q is —$NR^2R^{43}$, $R^2$ is —CH=$CPh_2$, $R^{43}$ is hydrogen and $Ar^1$ is 2-carbamoylphenyl;
n is 2, Q is —$NR^2R^{43}$, $R^2$ is hydrogen, $R^{43}$ is hydrogen, and $Ar^1$ is 1,8-napthylylene;

n is 1, Q is —NR$^2$R$^{43}$, R$^2$ is —CH=CPh$_2$, R$^{43}$ is hydrogen, and Ar$^1$ is 2-methoxycarbonylphenyl;

n is 1, Q is —NR$^2$R$^{43}$, R$^2$ is hydrogen, R$^{43}$ is hydrogen, and Ar$^1$ is 2-carboxyphenyl;

n is 1, Q is —NR$^2$R$^{43}$, R$^2$ is —CH=CPh$_2$, R$^{43}$ is hydrogen, and Ar$^1$ is 1-anthraquinonyl;

n is 1, Q is NR$^2$R$^{43}$, R$^2$ is —CH=CPh$_2$, R$^{43}$ is hydrogen, and Ar$^1$ is or wherein (III) is 6. The compound as recited in claim 1 wherein said first compound or said first monodentate neutral ligand is (V).

7. The compound as recited in claim 6 wherein:

m is 1, all of R$^8$, R$^4$, R$^5$, R$^6$ an R$^7$ are hydrogen, and both of R$^{10}$ are 2,6-diisopropylphenyl; or m is 1, all of R$^8$, R$^4$, R$^5$, R$^6$ an R$^7$ are hydrogen, and both of R$^{10}$ are cyclohexyl.

8. The compound as recited in claim 1 wherein said first compound or said first monodentate neutral ligand is (XVI).

9. The compound as recited in claim 8 wherein:

Ar$^2$ is 2-(N-2,2-diphenylethenylamino)phenyl and R$^{10}$ is hydrogen;

Ar$^2$ is phenyl and R$^{10}$ is 2,6-diisopropylphenyl;

Ar$^2$ is 2-pyridyl and R$^{10}$ is hydrogen; or

Ar$^2$ is 3-hydroxy-2-pyridyl and R$^{10}$ is hydrogen.

10. The compound as recited in claim 1 wherein said first compound or said first monodentate neutral ligand is (XVII).

11. The compound as recited in claim 10 wherein:

R$^{11}$ and R$^{15}$ are t-butyl and R$^{12}$, R$^{13}$ and R$^{14}$ are hydrogen;

R$^{11}$, R$^{13}$ and R$^{15}$ are t-butyl and R$^{12}$ and R$^{14}$ are hydrogen;

R$^{11}$ and R$^{15}$ are phenyl and R$^{12}$, R$^{13}$ and R$^{14}$ are hydrogen; or R$^{11}$ is t-butyl and R$^{12}$ and R$^{14}$ are hydrogen, R$^{13}$ is methoxy, and R$^{15}$ is 2-hydroxy-3-t-butyl-5-methoxyphenyl.

12. The compound as recited in claim 1 wherein said first compound or said first monodentate neutral ligand is (XVIII).

13. The compound as recited in claim 1 wherein said first compound or said first monodentate neutral ligand is (XIX).

14. The compound as recited in claim 1 wherein said first compound or said first monodentate neutral ligand is (XX) both of R$^{44}$ are phenyl.

15. The compound as recited in claim 14 wherein:

both of R$^{16}$ and R$^{17}$ are hydrogen; or both of R$^{16}$ and R$^{17}$ are acetyl.

16. The compound as recited in claim 1 wherein said first compound or said first monodentate neutral ligand is (XXI).

17. The compound as recited in claim 16 wherein Ar$^3$ is 2-aminophenyl.

18. The compound as recited in claim 1 wherein said first compound or said first monodentate neutral ligand is (XXII).

19. The compound as recited in claim 18 wherein R$^{18}$ and R$^{19}$ are both methyl or both hydrogen.

20. The compound as recited in claim 1 wherein said first compound or said first monodentate neutral ligand is (XXIII).

21. The compound as recited in claim 20 wherein Ar$^4$ is phenyl.

22. The compound as recited in claim 1 wherein said first compound or said first monodentate neutral ligand is (XXIV).

23. The compound as recited in claim 22 wherein both of Ar$^5$ and Ar$^6$ are phenyl or wherein both of Ar$^5$ and Ar$^6$ are cyclohexyl.

24. The compound as recited in claim 1 wherein said first compound or said first monodentate neutral ligand is (XXV).

25. The compound as recited in claim 1 wherein said first compound or said first monodentate neutral ligand is (XXVI).

26. The compound as recited in claim 25 wherein Ar$^7$ is p-tolyl or phenyl and Ar$^8$ is 2,6-diisopropylphenyl.

27. The compound as recited in claim 1 wherein said first compound or said first monodentate neutral ligand is (XXVII).

28. The compound as recited in claim 27 wherein:

Ar$^9$ and Ar$^{10}$ taken together are 1,8-naphthylylene; or

Ar$^9$ is —CO$_2$CH$_3$ and Ar$^{10}$ is

29. The compound as recited in claim 1 wherein said first compound or said first monodentate neutral ligand is (XXVIII).

30. The compound as recited in claim 29 wherein:

all of R$^{22}$, R$^{23}$ and R$^{24}$ are 2,4,6-trimethoxyphenyl;

both of R$^{22}$ and R$^{23}$ are 2,3,6-trimethoxyphenyl and R$^{24}$ is ethyl;

all of R$^{22}$, R$^{23}$ and R$^{24}$ are 2,6-dimethoxyphenyl; or both of R$^{22}$ and R$^{23}$ are 2,3,6-trimethoxyphenyl and R$^{24}$ is isopropyl.

31. The compound as recited in claim 29 wherein at least one of $R^{22}$, $R^{23}$ and $R^{24}$ is substituted and that a sum of σ and σ* constants for at least one of $R^{22}$, $R^{23}$ and $R^{24}$ is about −0.50 or less.

32. The compound as recited in claim 31 wherein $R^{24}$ is an aryl moiety, all of $R^{22}$, $R^{23}$ and $R^{24}$ are substituted, and said sum of said σ and σ* constants for each of $R^{22}$, $R^{23}$ and $R^{24}$ is about −0.50 or less.

33. A compound of the formula

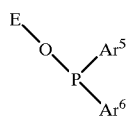

(XXIV)

wherein:

E is 2-thienyl or 2-furyl;

$Ar^5$ and $Ar^6$ are each independently hydrocarby.

34. The compound as recited in claim 33 wherein both of $Ar^5$ and $Ar^6$ are phenyl or wherein both of $Ar^5$ and $Ar^6$ are cyclohexyl.

35. The compound as recited in claim 1 wherein said first compound or said first monodentate neutral ligand is (XXXVI).

36. The compound as recited in claim 1 wherein (XXXVI) is

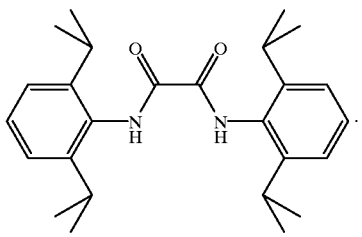

37. The compound as recited in claim 1 wherein said first compound or said first monodentate neutral ligand is (XXXVII).

38. The compound as recited in claim 37 wherein both of $R^8$ are aryl moieties and all of $R^4$, $R^5$, $R^6$, $R^7$ and $R^8$ are hydrogen.

39. The compound as recited in claim 1 wherein X is BAF.

40. The or compound as recited in claim 1 wherein r is 1.

41. The compound as recited in claim 1 wherein r is 0.

42. The compound as recited in claim 41 wherein (XXXIII) is a dimer with bridging $L^1$ ligands.

43. The compound as recited in claim 3 wherein:

n is 2

Q is —$CR^9$=$NR^3$;

$Ar^1$ is diphenylmethyl; $R^9$ is hydrogen and $R^3$ is selected from the group consisting of 2,6-diisopropylphenyl, 2-carbamoylphenyl, 2-methoxycarbonylphenyl, 1-anthraquinolyl, 2,6-dimethylphenyl and 1-fluoren-9-onyl.

44. The compound as recited in claim 1 wherein $L^3$ and $L^4$ taken together are a π-allyl group.

* * * * *